(12) United States Patent
Leonhardt et al.

(10) Patent No.: US 11,849,910 B2
(45) Date of Patent: Dec. 26, 2023

(54) METHODS, SYSTEMS, AND DEVICES FOR HEART VALVE DECALCIFICATION, REGENERATION, AND REPAIR

(71) Applicant: VALVUBLATOR INC., Mission Viejo, CA (US)

(72) Inventors: Howard J. Leonhardt, Mission Viejo, CA (US); Brett M. Burton, Erda, UT (US); Kapil K. Sharma, Salt Lake City, UT (US); Betty Vowles, West Bountiful, UT (US)

(73) Assignee: VALVUBLATOR INC., Playa Vista, CA (US)

( * ) Notice: Subject to any disclaimer, the term of this patent is extended or adjusted under 35 U.S.C. 154(b) by 274 days.

(21) Appl. No.: 16/842,683

(22) Filed: Apr. 7, 2020

(65) Prior Publication Data
US 2020/0229831 A1  Jul. 23, 2020

Related U.S. Application Data

(63) Continuation-in-part of application No. 15/812,760, filed on Nov. 14, 2017, now Pat. No. 10,960,206, (Continued)

(51) Int. Cl.
*A61B 17/22* (2006.01)
*A61F 2/24* (2006.01)

(52) U.S. Cl.
CPC ........ *A61B 17/2202* (2013.01); *A61F 2/2409* (2013.01); *A61F 2/2412* (2013.01);
(Continued)

(58) Field of Classification Search
CPC ...... A61B 17/2202; A61B 2017/22079; A61B 2017/22098; A61B 2217/007;
(Continued)

(56) References Cited

U.S. PATENT DOCUMENTS

D263,073 S   2/1982 Jonkers et al.
D273,893 S   5/1984 Weitzman
(Continued)

FOREIGN PATENT DOCUMENTS

AU   2019363173 A3   4/2020
CA   2685161 A1   10/2007
(Continued)

OTHER PUBLICATIONS

Messas et al. "Feasibility and Performance of Noninvasive Ultrasound Therapy in Patients With Severe Symptomatic Aortic Valve Stenosis: A First-in-Human Study. Circulation" Mar. 2, 2021;143(9):968-970. doi: 10.1161/CIRCULATIONAHA. 120.050672. Epub Jan. 25, 2021.
(Continued)

*Primary Examiner* — Mark W. Bockelman
(74) *Attorney, Agent, or Firm* — TraskBritt

(57) ABSTRACT

Methods of heart valve decalcification may include mechanically removing calcium deposits on a heart valve, and removing debris from the mechanical decalcification via suction. The mechanical removal of the calcium deposits may be accomplished with a burr and/or an ultrasonic device. In some embodiments, mechanical removal of the calcium deposits may be accomplished with a handheld mechanical decalcification device comprising a bur extending from a hand piece. A catheter system for removing plaque deposits from a heart valve may include at least one mechanical decalcification device configured for cleaning the edges of heart valve leaflets, and at least one active aspiration device. The at least one mechanical decalcification device may comprise a bur and/or an ultrasonic device. The system may additionally include a deployable net apparatus configured to encompass at least a portion of a heart valve.

20 Claims, 6 Drawing Sheets

Related U.S. Application Data which is a continuation-in-part of application No. 15/460,129, filed on Mar. 15, 2017, now Pat. No. 10,646,644.

(60) Provisional application No. 62/308,702, filed on Mar. 15, 2016, provisional application No. 62/363,012, filed on Jul. 15, 2016, provisional application No. 62/364,472, filed on Jul. 20, 2016, provisional application No. 62/375,271, filed on Aug. 15, 2016, provisional application No. 62/385,124, filed on Sep. 8, 2016, provisional application No. 62/454,521, filed on Feb. 3, 2017, provisional application No. 62/352,930, filed on Jun. 21, 2016, provisional application No. 62/831,083, filed on Apr. 8, 2019.

(52) U.S. Cl.
CPC ............ *A61B 2017/22079* (2013.01); *A61B 2017/22098* (2013.01); *A61B 2217/007* (2013.01)

(58) Field of Classification Search
CPC . A61B 17/22; A61B 17/32002; A61B 17/221; A61B 2017/00243; A61B 2017/22047; A61B 17/22012; A61B 2017/320004; A61F 2/2409; A61F 2/2412
See application file for complete search history.

(56) References Cited

U.S. PATENT DOCUMENTS

| | | |
|---|---|---|
| 4,622,952 A | 11/1986 | Gordon |
| 4,976,733 A | 12/1990 | Girardot |
| 5,135,478 A | 8/1992 | Sibalis |
| 5,211,622 A | 5/1993 | Liboff et al. |
| 5,295,958 A * | 3/1994 | Shturman ......... A61M 25/1002 606/159 |
| 5,543,318 A | 8/1996 | Smith et al. |
| 5,555,883 A | 9/1996 | Avitall |
| 5,693,029 A | 12/1997 | Leonhardt |
| 5,713,917 A | 2/1998 | Leonhardt et al. |
| 5,725,377 A | 3/1998 | Lemler et al. |
| 5,817,139 A | 10/1998 | Kasano |
| 5,957,949 A | 9/1999 | Leonhardt et al. |
| 6,047,700 A * | 4/2000 | Eggers ............... A61B 18/1492 606/41 |
| 6,344,052 B1 | 2/2002 | Greenan et al. |
| 6,618,625 B2 | 9/2003 | Silverstone |
| 6,957,106 B2 | 10/2005 | Schuler et al. |
| 6,988,004 B2 | 1/2006 | Kanno et al. |
| 7,029,276 B2 | 4/2006 | Mao |
| 7,136,699 B2 | 11/2006 | Palti |
| 7,341,062 B2 | 3/2008 | Chachques et al. |
| 7,483,749 B2 | 1/2009 | Leonhardt et al. |
| 7,686,799 B2 | 3/2010 | Leonhardt et al. |
| 7,881,784 B2 | 2/2011 | Pasricha et al. |
| 8,041,428 B2 | 10/2011 | Errico et al. |
| 8,133,267 B2 | 3/2012 | Leonhardt et al. |
| 8,166,976 B2 | 5/2012 | Webster et al. |
| 8,226,407 B2 | 7/2012 | Hanewinkel et al. |
| 8,465,533 B2 | 6/2013 | Palti |
| 8,534,289 B2 | 9/2013 | Hernandez |
| 8,639,361 B2 | 1/2014 | Nathanson |
| 8,646,455 B2 | 2/2014 | Webster et al. |
| 8,656,930 B2 | 2/2014 | Schuler et al. |
| 8,660,669 B2 | 2/2014 | Nemeh et al. |
| 8,738,144 B2 | 5/2014 | Schneider |
| 8,909,346 B2 | 12/2014 | Chalmers |
| 8,945,104 B2 | 2/2015 | Boone et al. |
| 9,032,964 B2 | 5/2015 | Schuler et al. |
| 9,173,811 B2 | 11/2015 | Greiner et al. |
| 9,533,170 B2 | 1/2017 | Dye et al. |
| 9,545,331 B2 | 1/2017 | Ingemarsson-Matzen |
| D778,449 S | 2/2017 | Ingemarsson-Matzen |
| 9,656,096 B2 | 5/2017 | Pilla |
| 9,662,184 B2 | 5/2017 | Lowe |
| 9,687,383 B2 | 6/2017 | Ingemarsson-Matzen |
| 9,707,403 B2 | 7/2017 | Schuler |
| 9,987,326 B2 | 6/2018 | Koeffler et al. |
| D832,447 S | 10/2018 | Wiffen |
| 10,543,119 B2 | 1/2020 | Ingemarsson-Matzen |
| 10,561,836 B2 | 2/2020 | Sama |
| D881,399 S | 4/2020 | Ingemarsson-Matzen |
| 10,646,644 B2 | 5/2020 | Leonhardt et al. |
| 10,960,206 B2 | 3/2021 | Leonhardt et al. |
| 11,058,536 B2 * | 7/2021 | Huber ..................... A61F 2/856 |
| 11,110,274 B2 | 9/2021 | Leonhardt |
| 2002/0143373 A1 | 10/2002 | Courtnage et al. |
| 2003/0032998 A1 | 2/2003 | Altman |
| 2003/0220556 A1 | 11/2003 | Porat et al. |
| 2004/0010231 A1 | 1/2004 | Leonhardt et al. |
| 2004/0115587 A1 | 6/2004 | Breining et al. |
| 2004/0147906 A1 | 7/2004 | Voyiazis et al. |
| 2004/0236238 A1 | 11/2004 | Schuler et al. |
| 2005/0171578 A1 | 8/2005 | Leonhardt |
| 2006/0030908 A1 | 2/2006 | Powell et al. |
| 2006/0100553 A1 | 5/2006 | Lodin |
| 2006/0116721 A1 | 6/2006 | Yun et al. |
| 2006/0195164 A1 | 8/2006 | Sondergaard et al. |
| 2007/0123758 A1 | 5/2007 | Miesel et al. |
| 2007/0167984 A1 | 7/2007 | Kieval et al. |
| 2007/0190028 A1 | 8/2007 | Qu et al. |
| 2007/0265680 A1 | 11/2007 | Liu et al. |
| 2008/0227046 A1 | 9/2008 | Lowe et al. |
| 2008/0243060 A1 | 10/2008 | Hartmann et al. |
| 2009/0132010 A1 | 5/2009 | Kronberg |
| 2009/0240304 A1 | 9/2009 | Blum et al. |
| 2010/0082027 A1 | 4/2010 | Chalmers |
| 2010/0184183 A1 | 7/2010 | Schussler et al. |
| 2010/0217148 A1 | 8/2010 | Binder |
| 2012/0156648 A1 | 6/2012 | Kaufman et al. |
| 2013/0253413 A1 | 9/2013 | Levine et al. |
| 2014/0023983 A1 | 1/2014 | Lowe et al. |
| 2014/0214115 A1 | 7/2014 | Greiner et al. |
| 2014/0214116 A1 | 7/2014 | Peterson et al. |
| 2014/0214124 A1 | 7/2014 | Greiner et al. |
| 2014/0214144 A1 | 7/2014 | Peterson et al. |
| 2014/0228910 A1 | 8/2014 | Schuler et al. |
| 2017/0028184 A1 | 2/2017 | Godden et al. |
| 2017/0036032 A1 | 2/2017 | Schuler et al. |
| 2017/0112983 A1 | 4/2017 | Thorne et al. |
| 2017/0266371 A1 | 9/2017 | Eonhardt et al. |
| 2017/0274206 A1 | 9/2017 | Leonhardt |
| 2018/0043159 A1 | 2/2018 | Hassan et al. |
| 2018/0064935 A1 | 3/2018 | Leonhardt et al. |
| 2018/0071135 A1 | 3/2018 | Ingemarsson-Matzen |
| 2018/0117322 A1 | 5/2018 | Chang et al. |
| 2018/0193646 A1 | 7/2018 | Fostick et al. |
| 2019/0015661 A1 | 1/2019 | Leonhardt et al. |
| 2019/0022389 A1 | 1/2019 | Leonhardt |
| 2019/0022396 A1 | 1/2019 | Leonhardt |
| 2019/0125932 A1 | 5/2019 | Leonhardt et al. |
| 2019/0255321 A1 | 8/2019 | Planard-Luong |
| 2019/0290541 A1 | 9/2019 | Greiner et al. |
| 2020/0030136 A1 | 1/2020 | Hernandez |
| 2020/0121984 A1 | 4/2020 | Sama |
| 2020/0289826 A1 | 9/2020 | Eonhardt |
| 2020/0324106 A1 | 10/2020 | Leonhardt |
| 2020/0330753 A1 | 10/2020 | Leonhardt et al. |
| 2021/0228870 A1 | 7/2021 | Leonhardt |

FOREIGN PATENT DOCUMENTS

| | | |
|---|---|---|
| EP | 0603451 A1 | 6/1994 |
| EP | 3291880 B1 | 7/2021 |
| GB | 2578310 A | 5/2020 |
| GB | 2578318 A | 5/2020 |
| JP | 2013-034881 A | 2/2013 |
| KR | 10-2007-0010908 A | 1/2007 |
| KR | 10-0726825 B1 | 6/2007 |
| WO | 92/17118 A1 | 10/1992 |
| WO | 2006/116728 A2 | 11/2006 |

(56) References Cited

FOREIGN PATENT DOCUMENTS

| WO | 2007/146187 A2 | 12/2007 |
|---|---|---|
| WO | 2008/145724 A1 | 12/2008 |
| WO | 2009/021535 A1 | 2/2009 |
| WO | 2011/016629 A2 | 2/2011 |
| WO | 2014/172693 A2 | 10/2014 |
| WO | 2016/135295 A1 | 9/2016 |
| WO | 2017/142948 A1 | 8/2017 |
| WO | 2020/079436 A3 | 4/2020 |
| WO | 2020/185622 A1 | 9/2020 |

OTHER PUBLICATIONS

Metro News "Bioelectricity: A shocking revolution in skincare?" Website accessed Aug. 4, 2021 https://metro.co.uk/2010/09/26/bioelectricity-a-shocking-revolution-in-skincare-523763/.

Miron "The Concept of Smart Tissue Regeneration with PRF" (Apr. 3, 2017) accessed Aug. 4, 2021 http://oasisdiscussions.ca/2017/04/03/prf/.

Mishra "Angiogenic neovessels promote tissue hypoxia," Proc. Natl. Acad. Sci. U. S. A. Sep. 20, 2016; 113(38): 10458-10460, published online Sep. 13, 2016; doi: 10.1073/pnas.1612427113.

Muratori et al. "The cytotoxic synergy of nanosecond electric pulses and low temperature leads to apoptosis" Sci Rep 6, 36835 (2016). https://doi.org/10.1038/srep36835.

Nacopoulos "Use of Platelet Rich Fibrin in Facial Aesthetics and Rejuvenation" (Jun. 2017) accessed Aug. 4, 2021 https://doi.org/10.1002/9781119406792.ch13.

Nature "Skin regeneration with insights" Nature 551, 141 (Nov. 2017) https://doi.org/10.1038/551141a.

Norton et al. "Bioelectric Perturbations of Bone: Research Directions and Clinical Applications" Angle Orthod (1984) 54 (1): 73-87.

Novack "Inflammatory osteoclasts, a different breed of bone eaters?" Arthritis Rheumatol. Dec. 2016; 68(12): 2834-2836. doi: 10.1002/art.39835.

Odell et al. "Anti-inflammatory Effects of Electronic Signal Treatment" Pain physician. 11. 891-907 (2008). 10.36076/ppj.2008/11/891.

Ojeh et al. "Stem Cells in Skin Regeneration, Wound Healing, and Their Clinical Applications" Int. J. Mol. Sci. (Oct. 2015), 16, ISSN 1422-0067 www.mdpi.com/journal/ijms.

Oranger et al. "Cellular Mechanisms of Multiple Myeloma Bone Disease" Clinical and Developmental Immunology vol. 2013, Article ID 289458, 11 pages http://dx.doi.org/10.1155/2013/289458.

Oyajobi "Multiple myeloma/hypercalcemia" Arthritis Research & Therapy vol. 9, Article No. S4 (2007).

Paulus "Cytokines and heart failure," Heart Fail. Manit. 2000; 1(2):50-6.

Payne et al. "Bioelectric Control of Metastasis in Solid Tumors" Bioelectricity vol. 1, No. 3, (Sep. 16, 2019) https://doi.org/10.1089/bioe.2019.0013.

Petrescu et al. "Platelet rich fibrin as a gingival tissue regeneration enhancer" Journal of Dental Sciences, https://doi.org/10.1016/j.jds.2020.08.014.

Petrusca et al. "Experimental investigation of thermal effects in HIFU-based external valvuloplasty with a non-spherical transducer, using high-resolution MR thermometry" Phys Med Biol. Sep. 7, 2009;54(17):5123-38. doi: 10.1088/0031-9155/54/17/004. Epub Aug. 6, 2009 (ABSTRACT).

Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from: http://www.intechopen.com/books/current-cancer-treatment-novel-beyond-conventional-approaches/electrotherapy-on-cancer-experiment-and-mathematical-modeling, 2011.

Puro et al."Bioelectric impact of pathological angiogenesis on vascular function," PNAS Aug. 30, 2016 113 (35) 9934-9939; published ahead of print Aug. 22, 2016 https://doi.org/10.1073/pnas.1604757113.

Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.

Raje et al. "Role of the RANK/RANKL Pathway in Multiple Myeloma" Clin Cancer Res 2019 25(1): 12-20; DOI:10.1158/1078-0432.CCR-18-1537.

RFA (radiofrequency ablation), Swedish Medical Imaging, 2 pages, author unknown, undated.

Rocha et al. "Ultrasensitive System for Electrophysiology of Cancer Cell Populations: A Review" Bioelectricity vol. 1, No. 3 (Published Online:Sep. 16, 2019) https://doi.org/10.1089/bioe.2019.0020.

Ronchetti et al. "Dermal alterations in patients with Wilson's disease treated with D-penicillamine" J Submicrosc Cytol Pathol (Jan. 1989) 21(1 ):131-9.

Santos et al. "Interferential electrical stimulation improves peripheral vasodilatation in healthy individuals" Braz J Phys Ther. May-Jun. 2013; 17(3):281-288.

Sartori et al. "Effects of Transcutaneous Electrical Nerve Stimulation in Autonomic Nervous System of Hypertensive Patients: A Randomized Controlled Trial" Current Hypertension Reviews, Apr. 2018, 14, 66-71.

Schimmel et al. "Neuroinflammation in traumatic brain injury: A chronic response to an acute injury" Brain Circ, 2017, 3(3):135-142.

Segura et al. "New Material Developed for Accelerated Skin Regeneration in Major Wounds" National Institute of Biomedical Imaging and Bioengineering (Dec. 2015) Accessed Aug. 4, 2021 https://www.newswise.com/articles/new-material-developed-for-accelerated-skin-regeneration-in-major-wounds?channel=.

Shimamura et al. "OPG/RANKL/RANK axis is a critical inflammatory signaling system in ischemic brain in mice." Proceedings of the National Academy of Sciences of the United States of America vol. 111,22 (2014): 8191-6. doi: 10.1073/pnas.1400544111.

Showkatbakhsh et al. "Effect of Intra-Canal Direct Current Electric Stimulation on Orthodontic Tooth Movement: An Experimental Study in Canines" Journal of Dental School 2016; 34(3): 157-67.

Showkatbakhsh et al. "The effect of pulsed electromagnetic fields on the acceleration of tooth movement." World J Orthod. 2010 Winter;11(4):e52-6.

Silva et al. "Engineered hydrogel-based matrices for skin wound healing" (Dec. 2016) In book: Wound Healing Biomaterials (pp. 227-250) DOI:10.1016/B978-1-78242-456-7.00011-8.

Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.

Singh et al. "3D Printing of Scaffold for Cells Delivery: Advances in Skin Tissue Engineering" Polymers (Jan. 2016), 8, 19; doi:10.3390/polym8010019.

Sisay et al. "The RANK/RANKL/OPG system in tumorigenesis and metastasis of cancer stem cell: potential targets for anticancer therapy" Onco Targets Ther. 2017; 10: 3801-3810.

Skardal "Amniotic Fluid Stem Cells for Wound Healing" Perinatal Stem Cells (Jul. 2014) Springer, New York, NY. https://doi.org/10.1007/978-1-4939-1118-9_2.

Skardal et al. "Bioprinted Amniotic Fluid-Derived Stem Cells Accelerate Healing of Large Skin Wounds" Stem Cells Translationalmedicine (Oct. 2012)1:792-802.

Su et al. "Klotho protein lowered in elderly hypertension" Int J Clin Exp Med (Aug. 2014) 7(8):2347-2350.

Sun "Regulation of Blood Pressure by Klotho" University of Oklahoma Health Sciences Center, Oklahoma City, OK, United States; accessed Jun. 2, 2021; https://grantome.com/grant/NIH/R01-HL102074-01A1.

Sun et al. "Amniotic fluid stem cells provide considerable advantages in epidermal regeneration: B7H4 creates a moderate inflammation microenvironment to promote wound repair" Scientific Reports (Jun. 2015) 5:11560, DOI: 10.1038/srep11560.

Sutherland et al. "Prolonged electrical stimulation of the nipples evokes intermittent milk ejection in the anaesthetised lactating rat," Exp Brain Res. 1987;66(1):29-34.

(56) References Cited

OTHER PUBLICATIONS

Takenaka et al. "Klotho Supplementation Attenuatesblood Pressure and Cyst Growth Inmouse Polycystic Kidney Disease" Journal of Hypertension: vol. 36—Issue—p. e76 (Jun. 2018).

Tan et al. "Bioelectric Perturbations in Orthodontic tooth movement" 2010 Journal of Dental Sciences & Research 1:1: pp. 41-49.

Tokyo Medical and Dental University "Rankl expressed by osteocytes has an important role in orthodontic tooth movement" Science Daily Oct. 20, 2017.

Tsang et al. "Large animal models of cardiovascular disease" Cell Biochemistry and Function (Feb. 2016) vol. 34, Issue 3 p. 113-132.

Tyler "Nature's Electric Potential: A Systematic Review of the Role of Bioelectricity in Wound Healing and Regenerative Processes in Animals, Humans, and Plants" Front. Physiol., (Sep. 2017) https://doi.org/10.3389/fphys.2017.00627.

Ueland et al. "Inflammatory cytokines as biomarkers in heart failure," Clinica Chimica Acta, vol. 443, Mar. 30, 2015, pp. 71-77; doi.org/10.1016/j.cca.2014.09.001.

Van Dam et al. "RANK/RANKL signaling inhibition may improve the effectiveness of checkpoint blockade in cancer treatment" Critical Reviews in Oncology/Hematology vol. 133, Jan. 2019, pp. 85-91.

Verna et al. "The rate and the type of orthodontic tooth movement is influenced by bone turnover in a rat model" European Journal of Orthodontics 22 (2000) 343-352.

Vig et al. "Advances in Skin Regeneration Using Tissue Engineering" Int. J. Mol. Sci. (Apr. 2017), 18, 789; doi:10.3390/ijms18040789.

Yamaguchi, "RANK/RANKL/OPG during orthodontic tooth movement", Orthod Craniofac Res. May 2009; 12(2):113-9. doi: 10.1111/j.1601-6343.2009.01444.x.

Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4(3):312-5 (Dec. 1999).

Yang et al., "Acupuncture for hypertension," Cochrane Database of Systematic Reviews, Available Online at <https://www.cochranelibrary.com/cdsr/doi/10.1002/14651858.CD008821.pub2/full >, (2018), 4 pages.

Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.

Yarbrough et al., "Specific Binding and Mineralization of Calcified Surfaces by Small Peptides," Calcified Tissue International, vol. 86, (2010), pp. 58-66.

Yu et al. "Association between inflammation and systolic blood pressure in RA compared to patients without RA" Arthritis Research & Therapy vol. 20, Article No. 107 (2018).

Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.

Zhang et al. "Exosomes derived from human embryonic mesenchymal stem cells promote osteochondral regeneration", Osteoarthritis and Cartilage, vol. 24, Issue 12, Dec. 2016, pp. 2135-2140.

Zhang et al., "Comparison of arterial stiffness in non-hypertensive and hypertensive population of various age groups," Jan. 24, 2018, 2 pages (Abstract Only).

Zhang et al., "Highly Stable and Reusable Imprinted Artificial Antibody Used for in Situ Detection and Disinfection of Pathogens," Chemical Science, vol. 6, (2015), pp. 2822-2826.

Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).

Villemain et al. Pulsed Cavitational Ultrasound Softening : A New Noninvasive Therapeutic Approach for Calcified Bioprosthetic Valve Stenosis' JACC: Basic to Translational Science vol. 2, Issue 4, Aug. 2017, pp. 372-383.

Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/S41551-017-0157-y.

Wei et al. "Nanofat-derived stem cells with platelet-rich fibrin improve facial contour remodeling and skin rejuvenation after autologous structural fat transplantation" Research Paper, Oncotarget (Jul. 2017) vol. 8, (No. 40), pp. 68542-68556.

Westermark et al. "Effect of externally applied focused acoustic energy on clot disruption in vitro" Clinical Science 97(1):67-71 (Jul. 1999); DOI:10.1042/CS19980379.

Wu et al. "MSC-exosome: A novel cell-free therapy for cutaneous regeneration" Cytotherapy, vol. 20, Issue 3, (Mar. 2018) pp. 291-301, https://www.sciencedirect.com/science/article/pii/S146532491730717X.

Wu et al. "Validation study toward measuring the mechanical properties of blood clots using resonant acoustic spectroscopy with optical vibrometry." Proceedings of SPIE—the International Society for Optical Engineering vol. 8214 (epub Feb. 2012): 82140G. doi:10.1117/12.906956.

Xiong et al. "Current understanding of neuroinflammation after traumatic brain injury and cell-based therapeutic opportunities" Chin J Traumatol. Jun. 2018; 21(3): 137-151. doi: 10.1016/j.cjtee.2018.02.003.

Yang "Effect RANKL Produced by Periodontal Ligament Cells on Orthodontic Tooth Movement" (2016) Dental Theses. Paper 13.

Yang et al. "Effect of Amniotic Fluid Stem Cells and Amniotic Fluid Cells on the Wound Healing Process in a White Rat Model" APS, vol. 40, No. 5 (Sep. 2013).

Yildirimer et al. "Skin regeneration scaffolds: a multimodal bottom-up approach" Trends in Biotechnology, Dec. 2012, vol. 30, No. 12, pp. 638-648.

Yoon et al. "Skin Regeneration Effect and Chemical Composition of Essential Oil from Artemisia montana" Natural Product Communications (Sep. 2014) vol. 9, No. 11, pp. 1619-1622.

Yu et al. "Effects and mechanisms of a microcurrent dressing on skin wound healing: a review" Military Medical Research (Nov. 2014) 1:24 http://www.mmrjournal.org/content/1/1/24.

Yuan et al. "Electrical stimulation enhances cell migration and integrative repair in the meniscus" Sci Rep 4, 3674 (2014). https://doi.org/10.1038/srep03674.

Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.

Zaske "Discovery enables adult skin to regenerate like a newborn's" Medical Research, accessed Aug. 4, 2021 https://medicalxpress-com.cdn.ampproject.org/c/s/medicalxpress.com/news/2020-09-discovery-enables-adult-skin-regenerate.amp.

Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).

Zhang et al. "Therapeutic potential of stem cells in skin repair and regeneration" Chinese Journal of Traumatology (Apr. 2008) 11(4):209-221.

Zhao et al. "Local osteoprotegerin gene transfer inhibits relapse of orthodontic tooth movement." Am J Orthod Dentofacial Orthop. Jan. 2012; 141(1):30-40. doi: 10.1016/j.ajodo.2011.06.035.

Zhong et al. "TKI-31 inhibits angiogenesis by combined suppression signaling pathway of VEGFR2 and PDGFRbeta" Cancer Biology & Therapy 5:3, 323-330, Mar. 2006.

Zhou et al. "Klotho Ameliorates Kidney Injury and Fibrosis and Normalizes Blood Pressure by Targeting the Renin-Angiotensin System" The American Journal of Pathology, vol. 185, No. 12, Dec. 2015.

(56) References Cited

OTHER PUBLICATIONS

Zhou et al. "Klotho Gene Deficiency Causes Salt-Sensitive Hypertension via Monocyte Chemotactic Protein-1/CC Chemokine Receptor 2-Mediated inflammation" J Am Soc Nephrol 26: 121-132, 2015 (Accepted Apr. 2014).
Zimmerman et al. "Cancer cell proliferation is inhibited by specific modulation frequencies" Br J Cancer. Jan. 17, 2012;106(2):307-13. doi: 10.1038/bjc.2011.523. Epub Dec. 1, 2011. PMID: 22134506; PMCID: PMC3261663.
Zimmerman et al. "Targeted treatment of cancer with radiofrequency electromagnetic fields amplitude-modulated at tumor-specific frequencies" Chin J Cancer. Nov. 2013;32(11):573-81. doi: 10.5732/cjc.013.10177. PMID: 24206915; PMCID: PMC3845545.
Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.
Almpani et al., "Nonsurgical Methods for the Acceleration of the Orthodontic Tooth Movement", Tooth Movement. Fronl Oral Biol., vol. 18, pp. 80-91 (Karger, Basel, CH 2016) (DOL10.1159/000382048), Published online: Nov. 24, 2015.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.0rg/10.1155/2013/105873.
Aubert et al. "A new ultrasonic process for a renewal of aortic valve decalcification" Cardiovascular Ultrasound 2006, 4:2 doi:10.1186/1476-7120-4-2.
Aydin et al., "Focusing of Electromagnetic Waves by a Left-Handed Metamaterial Flat Lens," vol. 13, (2005), pp. 8753-8759.
Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 | vol. 5 | Article 196.
Banerjee, P. "Electrical muscle stimulation for chronic heart failure: an alternative tool for exercise training?" Curr Heart Fail Rep., 7(2):52-8. doi: 10.1007/s11897-010-0013-9 (Jun. 2010).
Bang et al., "Attenuation of Hypertension by C-Fiber Stimulation of the Human Median Nerve and the Concept-Based Novel Device," Scientific Reports, vol. 8, (2018), 12 pages.
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
Barker et al., "A Formidable Foe is Sabotaging Your Results: What You Should Know About Biofilms and Wound Healing," Plastic and Reconstructive Surgery, vol. 139, (2017), pp. 1184e-1194e.
Beitelshees et al. "CXCL5 polymorphisms are associated with variable blood pressure in cardiovascular disease-free adults" Hum Genomics. 2012; 6(1): 9.
Bioleohardnew, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.
Blood Vessels Hold Key To Thicker Hair Growth, https://www.sciencedaily.com/releases/2001/02/010215074636.htm(Feb. 2001).
Borden et al., "Electric Current-Induced Detachment of *Staphylococcus epidermidis* Biofilms from Surgical Stainless Steel," Applied and Environmental Microbiology, vol. 70, (2004), pp. 6871-6874.
Borgobello, B. "FDA approves the treatment of brain tumors with electrical fields," New Atlas, http://newatlas.com/treatment-of-brain-tumors-with-electrical-fields/21433/(Feb. 13, 2012), last visited Sep. 12, 2018.
Bradshaw et al. "Designer self-assembling hydrogel scaffolds can impact skin cell proliferation and migration" Nature Scientific Reports, vol. 4, Article No. 6903 (2014).
Brooks et al. "Bioelectric impedance predicts total body water, blood pressure, and heart rate during hemodialysis in children and adolescents" J. Ren Nutr., 18(3):304-311 (May 2008); doi: 10.1053/j.jm.2007.11.008.

Cai et al., "Intermedin Inhibits Vascular Calcification by Increasing the Level of Matrix (Gamma)-Carboxyglutamic Acid Protein," Cardiovascular Research, vol. 85, (2010), pp. 864-873.
Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.
Caubet et al., "A Radio Frequency Electric Current Enhances Antibiotic Efficacy Against Bacterial Biofilms," Antimicrobial Agents and Chemotherapy, vol. 48, (2004), vol. 4662-4664.
Cerrada et al. "Hypoxia-Inducible Factor 1 Alpha Contributes to Cardiac Healing in Mesenchymal Stem Cells-Mediated Cardiac Repair," Stem Cells and Development, 22(3): 501-511 (2013).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Chang et al. Effect of Pulse-Burst Electromagnetic Field Stimulation on Osteoblast Cell Activities; Bioelectromagnetics 25:457-465 (2004).
Chernet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA.117.10560.) Downloaded from http://ahajournals.org by on Apr. 24, 2020 (9 pages).
Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Chen et al., "The Role and Mechanism of (Alpha)-Klotho in the Calcification of Rat Aortic Vascular Smooth Muscle Cells," BioMed Research International, vol. 2015, (2015), 7 pages.
Chen et al., "The Strategy to Prevent and Regress the Vascular Calcification in Dialysis Patients," BioMed Research International, vol. 2017, (2017), 11 pages.
Chen et al., Efficacy and Safety of Acupuncture for Essential Hypertension: A Meta-Analysis, Medical Science Monitor, vol. 24, (2018), pp. 2946-2969.
Chiang et al., "Silver-Palladium Surfaces Inhibit Biofilm Formation," Applied and Environmental Microbiology, vol. 75, (2009), pp. 1674-1678.
Collette et al., "Measurement of the local aortic stiffness by a non-invasive bioelectrical impedance technique," in Medical & Biological Engineering, vol. 49, No. 4, Feb. 2011, pp. 431-439, Available online at <https://www.ncbi.nlm.nih.gov/pubmed/21286830>, 1 page (Abstract Only).
Collins "Bioelectric Signals Can Be Used to Detect Early Cancer," Tufts News, http://now.tufts.edu/news-releases/bioelectric-signals-used-detect-early-cancer (Feb. 1, 2013).
Columbia "Implant Procedure Concepts—Pacemaker, ICD and CRT Overview," columbia.edu/itc/hs/medical/hickey/docs/Pacemaker,%20ICD%20and%20CRT%200verview%20022007.pdf, last risited Sep. 12, 2018.
Control of Hair Growth by a Growth Factor Protein, http://www.hairloss-reversible.com/control-of-hair-growth-by-a-growth-factor-protein/.
Control of pelage hair follicle development and cycling by complex interactions between follistatin and activin, FASEB J (Jan. 2, 2003).
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Costerton et al., "The Application of Biofilm Science to the Study and Control of Chronic Bacterial Infections," The Journal of Clinical Investigation, vol. 112, (2003), pp. 1466-1477.

(56) References Cited

OTHER PUBLICATIONS

Cowburn et al. "HIF isoforms in the skin differentially regulate systemic arterial pressure" Proc Natl Acad Sci U S A. Oct. 22, 2013; 110(43): 17570-17575.

Delcaru et al., "Microbial Biofilms in Urinary Tract Infections and Prostatitis: Etiology, Pathogenicity, and Combating strategies," Pathogens, vol. 5, (2016), 12 pages.

Dibart et al. "Tissue response during Piezocision-assisted tooth movement: a histological study in rats", Eur J Orthod (2014) 36 (4): 457-464; DOI: https://doi.org/10.1093/ejo/cjt079.

Dietrich et al. "Decalcification of the mitral annulus: surgical experience in 81 patients" Thorac Cardiovasc Surg. Oct. 2006;54(7):464-7 (Abstract Only).

Dong-Hwan Kim et al., The effects of electrical current from a micro-electrical device on tooth movement, Korean Orthod., Oct. 2008, 38(5):337-346.

Ehrlich et al., "Engineering Approaches for the Detection and Control of Orthopaedic Biofilm Infections," Clinical Orthopaedics and Related Research, vol. 437, (2005), pp. 59-66.

Elastatropin(Registered) in Scalp & Hair Conditioning https://www.proteingenomics.com/haircare.html.

Electric Tumor Treatment Fields, No. 0827 Policy, http://www.aetna.com/cpb/medical/data/800_899/0827.html (Nov. 18, 2016).

Electrical brain stimulation could support stroke recovery https://www.sciencedaily.com/releases/2016/03/160316151108.htm (Mar. 16, 2016).

Ellis, Marie "Cure for baldness? Stem cells bring hope" http://www.medicalnewstoday.com/articles/271898.php.

Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.

Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.

Abdel-Rehim "Change of serum klotho protein and its relationship with endothelial dysfunction, oxidative stress and arterial aging in essential hypertensive patients" J Kidney 2018, vol. 4 (Dec. 2018).

Ahrens et al. "Klotho expression is a prerequisite for proper muscle stem cell function and regeneration of skeletal muscle" Ahrens et al. Skeletal Muscle (Jul. 2018) 8:20 pp. 1-14.

Akbari ei al. "Association of Klotho gene polymorphism with hypertension and coronary artery disease in an Iranian population" BMC Cardiovascular Disorders (Dec. 2018) 18:237.

Andersson et al. "Drinking, antidiuresis and milk ejection from electrical stimulation within the hypothalamus of the goat," Acta Physiol Scand. Dec. 31, 1955; 35(2):191-201; DOI: 10.1111/j.1748-1716.1955.tb01277.x.

Ando et al."RANKL/RANK/OPG: key therapeutic target in bone oncology" Curr Drug Discov Technol. Sep. 2008; 5(3): 263-268.

Aronowitz et al. "Mechanical versus enzymatic isolation of stromal vascular fraction cells from adipose tissue" SpringerPlus (2015) 4:713 DOI 10.1186/s40064-015-1509-2.

ASPS, "Stem Cell Treatments 'Go Deep' to RegenerateSun-Damaged Skin" Article, American Society of Plastic Surgeons (May 27, 2020) 4 pages.

Atkinson et al. "Bioelectric Properties of the Tooth" 1969 vol. 48 issue: 5, pp. 789-794.

Banerjee et al. "MicroRNAs in Skin and Wound Healing" Methods Mol Biol. 2013; 936: 343-356, Author manuscript (Mar. 2015 ).

Barnhill "It's Electric! All About Microcurrent Facials" accessed Aug. 4, 2021, https://intothegloss.com/2016/04/microcurrent-treatment/.

Basu et al. "Exosomes for repair, regeneration and rejuvenation" Expert Opinion on Biological Therapy, 16:4, 489-506, DOI: 10.1517/14712598.2016.1131976.

Beebe et al. "Bioelectric Applications for Treatment of Melanoma," Cancers (Basel). Sep. 2010; 2(3): 1731-1770, published online Sep. 27, 2010; doi: 10.3390/cancers20317.

Berman "Suzanne Somers' Experimental Breast Reconstruction" Medpage Today, Feb. 7, 2012, www.medpagetoday.com > blogs > celebritydiagnosis.

Beugels et al. "Electrical stimulation promotes the angiogenic potential of adipose-derived stem cells" Scientific Reports (Aug. 2019) 9:12076.

Bi et al. "Key Triggers of Osteoclast-Related Diseases and Available Strategies for Targeted Therapies: A Review" Front Med (Lausanne). 2017; 4: 234. doi: 0.3389/fmed.2017.00234.

Blum "Role of cytokines in heart failure," American Heart Journal, vol. 135, Issue 2, Feb. 1998, pp. 181-186; doi.org/10.1016/S0002-8703(98)70080-8.

Botchkareva "MicroRNA/mRNA regulatory networks in the control of skin development and regeneration" Cell Cycle 11:3, 468-474; (Feb. 2012) Landes Bioscience.

Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11 Imaging and Bioengineering, Dec. 17, 2015).

Buckle et al. "Soluble Rank Ligand Produced by Myeloma Cells Causes Generalised Bone Loss in Multiple Myeloma" PLOS One. 2012; 7(8): e41127. doi: 10.1371/joumal.pone.0041127 PMCID: PMC3430669.

CalXStars Business Accelerator, Inc.—WEBSITE—Justia Patents—Mar. 15, 2017—US Patent Application for Stimulator, Pump & Composition Patent Application (Application #20170266371) https://protect-us.mimecast.com/s/tSaBCxkVlwuDr61CvMWbF?domain=patents.justia.com.

Campbell et al. "Electrical stimulation to optimize cardioprotective exosomes from cardiac stem cells" Med Hypotheses. Mar. 2016; 88:6-9. doi: 10.1016/j.mehy.2015.12.022. Epub Jan. 11, 2016.

Carboni ei al. "An initial study on the effect of functional electrical stimulation in erectile dysfunction: a randomized controlled trial" IJIR: Your Sexual Medicine Journal (May 2018) 30:97-101.

Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).

Chaikin et al. "Microcurrent stimulation in the treatment of dry and wet macular degeneration" Clinical Ophthalmology 2015:9 2345-2353 (Dec. 2015).

Chen et al. "Beyond anti-VEGF: dual-targeting antiangiogenic and antiproliferative therapy" Am J Transl Res. 2013;5(4):393-403 Published May 24, 2013.

Chen et al. "Nanosecond Pulsed Electric Field (nsPEF) Ablation as an Alternative or Adjunct to Surgery for Treatment of Cancer" Chen et al., Surgery Curr Res 2013, S12 DOI: 10.4172/2161-1076.S12-005.

Choi et al. "Exosomes from human adipose-derived stem cells promote proliferation and migration of skin fibroblasts" Experimental Dermatology. (Sep. 2017) 1-3.

Christouls et al. "Pathogenesis and Management of Myeloma Bone Disease" Expert Rev Hematol. 2009; 2(4):385-398.

Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.

Corrigan et al. "Neurogenic inflammation after traumatic brain injury and its potentiation of classical inflammation", Journal of Neuroinflammation, 2016, 13:264; doi://doi.org/10.1186/s12974-016-0738-9.

Costa et al. "Selecting patients for cytotoxic therapies in gastroenteropancreatic neuroendocrine tumours" Best Pract Res Clin Gastroenterol. Dec. 2012;26(6):843-54. doi: 10.1016/j.bpg.2012.12.001. PMID: 23582923.

Costa et al. "Treatment of advanced hepatocellular carcinoma with very low levels of amplitude-modulated electromagnetic fields" Br J Cancer. Aug. 23, 2011;105(5):640-8. doi: 10.1038/bjc.2011.292. Epub Aug. 9, 2011. PMID: 21829195; PMCID: PMC3188936.

Cross ei al. "Milk Ejection following Electrical Stimulation of the Pituitary Stalk in Rabbits," Nature 166, 994-995 (Dec. 9, 1950); doi:10.1038/166994b0 (Abstract Only).

(56) References Cited

OTHER PUBLICATIONS

Dai ei al. "Nanosecond Pulsed Electric Fields Enhance the Antitumour Effects of the mTOR Inhibitor Everolimus against Melanoma," Scientific Reports vol. 7, Article No. 39597 (2017).

Desai et al. "Use of Platelet-Rich Fibrin over Skin Wounds: Modified Secondary Intention Healing" Modified secondary intention healing. J Cutan Aesthet Surg (Jan-Mar. 2013) vol. 6, pp. 35-37.

Deswal ei al. "Cytokines and Cytokine Receptors in Advanced Heart Failure An Analysis of the Cytokine Database from the Vesnarinone Trial (VEST)," Circulation. 2001 ;103:2055-2059;.// doi.org/10.1161/01. CIR.103.16.2055.

Dimensija "PRF Injections Forprf Forskin Rejuvenationskin Rejuvenationand Tissueand Tissueregenerationregeneration" accessed Aug. 4, 2021, https://dimensija.Iv/news/prf-injekcijas-adas-atjaunosanai-un-audu-regeneracijai?lang=en.

Duscher et al. "Stem Cells in Wound Healing: The Future of Regenerative Medicine? A Mini-Review" (May 2015) Stem Cells in Wound Healing, Gerontology 2016;62:216-225.

El-Bialy et al. "Effect of Low Intensity Pulsed Ultrasound (LIPUS) on Tooth Movement and Root Resorption: A Prospective Multi-Center Randomized Controlled Trial" J. Clin. Med. 2020, 9, 804; doi:10.3390/jcm9030804.

Fallon "The obvious next step in the evolution of natural rejuvenation" Article (Aug. 2017) (accessed Aug. 4, 2021) https://www.newbeauty.com/platelet-rich-fibrin-skin-rejuvenation-prf/.

FDA "Same Surgical Procedure Exception under 21 CFR 1271.15(b): Questions and Answers Regarding the Scope of the Exception-Guidance for Industry" U.S. Department of Health and Human Services, Food and Drug Administration, Center for Biologics Evaluation and Research, Nov. 2017.

Ferrucci, D. A. "Introduction to This is Watson'," in IBM Journal of Research and Development, vol. 56, No. 3.4, pp. 1:1-1:15, May-Jun. 2012. DOI: 10.1147/JRD.2012.2184356.

Fili et al. "Therapeutic implications of osteoprotegerin" Cancer Cell International vol. 9, Article No. 26 (2009).

Fonseca et al. "Electrical stimulation: Complementary therapy to improve the performance of grafts in bone defects?" Journal of Biomedical Materials Research Part B: Applied Biomaterials 2018 vol. 000b, Issue 0.

Fujiya et al. "Microcurrent Electrical Neuromuscular Stimulation Facilitates Regeneration of Injured Skeletal Muscle in Mice" Journal of Sports Science and Medicine (Jun. 2015) 14, 297-303.

Gavira et al. "Repealed implantation of skeletal myoblast in a swine model of chronic myocardial infarction," Eur. Heart J., 31(8): 1013-1021. doi: 10.1093/eurheartj/ehp342 (2010).

Ge et al. "The aging skin microenvironment dictates stem cell behavior" PNAS (Mar. 2020), vol. 117, No. 10, pp. 5339-5350.

Ghazalian et al. "Effects of whole-body vibration training on fibrinolytic and coagulative factors in healthy young men." Journal of Research in Medical Sciences: the official journal of Isfahan University of Medical Sciences vol. 19,10 (Oct. 2014): 982-986.

Goldberg et al. "Skin Rejuvenation with Non-Invasive Pulsed Electric Fields" Sci Rep 5, 10187 (May 2015).

Goranov et al. "Bone Lesions in Multiple Myeloma—The OPG/RANK-ligand System" Folia Med (Plovdiv). 2004; 46(3): 5-11 (Abstract Only).

Dahm et al. "Decalcification of the aortic valve does not prevent early recalcification" J Heart Valve Dis., 9(1):21-6 (Jan. 2000).

Goswami et al. "Osteoprotegerin rich tumor microenvironment: implications in breast cancer" Oncotarget. Jul. 5, 2016; 7(27):42777-42791.

Gullestad et al. "Inflammatory cytokines in heart failure: mediators and markers," Cardiology. 2012;122(1):23-35. doi: 10.1159/000338166. Epub Jun. 12, 2012.

Gurbax et al. "Accelerated Orthodontic Tooth Movement: A Review" mod Res Dent. 1(2). MRD.000508. 2017. DOI: 10.31031/MRD 2017.01.000508.

Hamzelou et al. "Cancer reversed in frogs by hacking cells' electricity with light," New Scientist This Week, Mar. 16, 2016.

Holen et al. Role of Osteoprotegerin (OPG) in Cancer Clin Sci (Lond). Mar. 2006; 110(3):279-91. doi: 10.1042/CS20050175.

Horsburgh et al. "MicroRNAs in the skin; role in development, homeostasis, and regeneration" Clin Sci (Lond) (Jul.-Aug. 2017) 131 (15): 1923-1940.

Hu et al. "Exosomes derived from human adipose mesenchymal stem cells accelerates cutaneous wound healing via optimizing the characteristics of fibroblasts", Nature Scientific Reports, vol. 6, Article No. 32993 (2016).

Hudson et al. "Local delivery of recombinant osteoprotegerin enhances postorthodontic tooth stability" Calcif Tissue Int. Apr. 2012; 90(4):330-42. doi: 10.1007/s00223-012-9579-4.

Hunckler et al. "A current affair: electrotherapy in wound healing" Journal of Multidisciplinary Healthcare (Apr. 2017)10 179-194.

Iglesias-Linares et al. "The use of gene therapy vs. corticotomy surgery in accelerating orthodontic tooth movement." Orthod Craniofac Res. Aug. 2011; 14(3):138-48. doi: 10.1111/j.1601-6343.2011.01519.x.

Infante et al. "RANKL/RANK/OPG system beyond bone remodeling: involvement in breast cancer and clinical perspectives" Journal of Experimental & Clinical Cancer Research (2019) 38:12. https://doi.0rg/10.1186/s13046-018-1001-2.

International Search Report for International Application No. PCT/US2019/025177, dated Sep. 3, 2019, 3 pages.

International Written Opinion for International Application No. PCT/US2019/025177, dated Sep. 3, 2019, 5 pages.

Itatani et al. "Resistance to Anti-Angiogenic Therapy in Cancer-Alterations to Anti-VEGF Pathway" Int J Mol Sci. Apr. 18, 2018;19(4):1232. doi: 10.3390/ijms19041232. PMID: 29670046; PMCID: PMC5979390.

Ivanyi "How Microcurrent Treatments Improve Acne" Envision Acne & Skin Care Center, website accessed Aug. 4, 2021, https://envisionacnecenter.com/microcurrent-treatments-improve-acne/.

Jamal et al. "Klotho, Hypertension and Arterial Stiffness: A Review" Austin J Nephrol Hypertens.(Jul. 2019) 6(2): 1082.

JCCR "Emerging roles of klotho in cardiovascular diseases%5D" Accessed Jun. 2, 2021 https://medcraveonline.com/JCCR/emerging-roles-of-klotho-in-cardiovascular-diseases.html%5D.

Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.

John et al. "Growth Factors in Skin Care—Series Introduction" (Mar. 2015) website accessed Aug. 4, 2021 http://barefacedtruth.com/2015/03/28/growth-factors-skin-care-introduction/.

John et al. "Growth Factors in Skin Care—Series Introduction" BareFacedTruth (Mar. 2015) 9 pages.

Jouybar et al. "Enhanced Skin Regeneration by Herbal Extract-Coaled Poly-L-Lactic Acid Nanofibrous Scaffold" Artif Organs. Nov. 2017; 41(11):E296-E307. doi: 10.1111/aor.12926 (Abstract Only).

Jung et al. "Prospective 1-Year Follow-Up Study of Breast Augmentation by Cell-Assisted Lipotransfer" Aesthetic Surgery Journal 2016, vol. 36(2) 179-190 @ 2015 The American Society for Aesthetic Plastic Surgery, Inc.

Kawagishi et al. S"onic hedgehog signaling regulates the mammalian cardiac regenerative response" Journal of Molecular and Cellular Cardiology; vol. 123, p. 180-184 (Oct. 2018).

Keunen et al. "Anti-VEGF treatment reduces blood supply and increases tumor cell invasion in glioblastoma," Proc. Natl. Acad. Sci. U.S. A. Mar. 1, 2011; 108(9):3749-3754, published online Feb. 14, 2011; doi: 10.1073/pnas.1014480108.

Kim et al. "Hyaluronate—Epidermal Growth Factor Conjugate for Skin WoundHealing and Regeneration" Biomacromolecules (Oct. 2016) 17 , 11, 3694-3705 (Abstract Only) Publication Date : Oct. 24, 2016.

Kim et al. "Picking Winners and Losers: Cell Competition in Tissue Development and Homeostasis" vol. 36, Issue 7, p. 490-498, Jul. 1, 2020 (Abstract Only).

Kondo et al. "Types of tooth movement, bodily or tipping, do not affect the displacement of the tooth's center of resistance but do affect the alveolar bone resorption" Angle Orthod Jul. 2017; 87(4):563-569.

(56) References Cited

OTHER PUBLICATIONS

Lam et al. "Mesenchymal stem cell therapies for skin repair and regeneration" J Dermat Cosmetol. (Aug. 2017) vol. 1, Issue 3, pp. 62?64.

Lamoureux et al. "Therapeutic Relevance of Osteoprotegerin Gene Therapy in Osteosarcoma: Blockade of the Vicious Cycle between Tumor Cell Proliferation and Bone Resorption" Cancer Res 1 2007 67(15):7308-7318; DOI: 10.1158/0008-5472.CAN-06-4130.

Landau et al. "Review: Proposed Methods to Improve the Survival of Adipose Tissue in Autologous Fat Grafting" Plast Reconstr Surg Glob Open. 2018;6(8):e1870. Published Aug. 3, 2018. doi:10.1097/GOX.0000000000001870.

Lanzetto et al. "Fundamental principles of an anti-VEGF treatment regimem optimal application of intravitreal anti-vascular endothelial growth factor therapy of macular diseases," Graefes Arch. Clin. Exp. Ophthalmol. 2017; 255(7)11259-1273 (published online May 19, 2017); doii 10.1007/s00417-017-3647-4.

Ledzewicz et al. "Analysis of optimal controls for a mathematical model of tumor anti-angiogenesis" Optim. Control Appl. Meth. 2006; 00:1-16.

Leonhardt "PressureStim Blood Pressure Control" accessed Jun. 2, 2021, https://pressurestim.com.

Leonhardt "PressureStim Receives IRB Approval to Launch Bioelectric Hypertension Treatment Clinical Study" Accessed Jun. 2, 2021, https://www.prdistribution.com/news/pressurestim-receives-irb-approval-to-launch-bioelectric-hypertension-treatment-clinical-study-2.html?fbclid=IwAR28Dh97RAKXXHrfgUONKW1pk-MWyeF_ibUlpQc_2XEN32C6sS%E2%80%A6.

Liang et al. "Therapeutic effect of low-intensity pulsed ultrasound on temporomandibular joint injury induced by chronic sleep deprivation in rats" Am J Transl Res. 2019; 11(6): 3328-3340.

Liesz et al. Editorial: Mechanisms of neuroinflammation and inflammatory neurodegeneration in acute brain injury Front. Cell. Neurosci., 2015. doi://doi.org/10.3389/fncel.2015.00300.

LifeWave X39™ Patches; website access Aug. 4, 2021 https://lifewave.com/corporphan/store/product/39000.022.009/.

Lobo-Silva et al. "Balancing the immune response in the brain: IL-10 and its regulation," Journal of Neuroinflammation, 13:297 (2016); doi.org/10.1186/s12974-016-0763-8.

Loizzi et al. "Biological Pathways Involved in Tumor Angiogenesis and Bevacizumab Based Anti-Angiogenic Therapy with Special References to Ovarian Cancer" International Journal of Molecular Sciences. (Sep. 2017); 18(9):1967. https://doi.org/10.3390/ijms18091967.

Lopes-Bastos et al. "Tumour-Endothelial Cell Communications: Important and Indispensable Mediators of Tumour Angiogenesis" Anticancer Research Mar. 2016, 36 (3) 1119-1126.

Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.

Maltese et al. "The Putative Role of the Antiageing Protein Klotho in Cardiovascular and Renal Disease" Hindawi Publishing Corporation International Journal of Hypertension, (Sep. 2011) vol. 2012, Article ID 757469, 5 pages.

Mann, "Innate Immunity and the Failing Heart: The Cytokine Hypothesis Revisited," Circ. Res. Mar. 27, 2015; 116(7): 1254-1268.

Mao et al. "13-Hydrogel fibrous scaffolds for accelerated wound healing" In Woodhead Publishing Series in Biomaterials, Electrofluidodynamic Technologies (EFDTs) for Biomaterials and Medical Devices, Woodhead Publishing, (Jan. 2018) pp. 251-274, ISBN 9780081017456, https://doi.org/10.1016/B978-0-08-101745-6.00013-X.

Martin "Historically significant events in the discovery of RANK/RANKL/OPG" World J Orthop. Oct. 18, 2013; 4(4): 186-197. doi: 10.5312/wjo.v4.i4.186.

Matsumori, "Cytokines and Heart Failure: Pathophysiological Roles and Therapeutic Implications," Heart Failure, Springer, Tokyo; doi.org/10.1007/978-4-431-68331-5_3.

McGrath "OPG/RANKL/RANK Pathway as a Therapeutic Target in Cancer" Journal of Thoracic Oncology, Sep. 2011 6(9): 1468-1473.

McMillan "Longevity Protein' Enables Muscle Regeneration In Old Mice" accesses Jun. 2, 2021; https://www.forbes.com/sites/fionamcmillan/2018/11/25/longevity-protein-enables-muscle-regeneration-in-old-mice/?sh=51709d57392a.

Meadows et al. "Anti-VEGF Therapies in the Clinic," Cold Spring Harb. Perspect. Med. Oct. 2012; 2(10): a006577: doi: 10.1101/cshperspect.a006577.

Mei al. "Combined effect of mhTGF-β1 and rhPDGF-BB on the expression of Pyk2 protein and mRNA gene during orthodontic tooth movement in SD rats" Shanghai Kou Qiang Yi Xue. Oct. 2019;28(5):472-477. Chinese. PMID: 32274476.

Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/ (Aug. 24, 2015).

Robert Ferris, "Battle against baldness turns to stem cells" http://www.cnbc.com/2015/01/29/studies-indicate-its-possible-to-use-stem-cells-to-cure-baldness.html (Jan. 29, 2015).

Roy et al., "Disposable Patterned Electroceutical Dressing (PED-10) Is Safe for Treatment of Open Clinical Chronic Wounds," Advances in Wound Care, vol. 8, (1019), pp. 149-159.

Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages) Abstract Only.

Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.

Sahoo and Losordo "Exosomes and Cardiac Repair After Myocardial Infarction," Circulation Research, 114:333-344 (Jan. 16, 2014).

Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).

Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.

Schardong et al., "Intradialytic neuromuscular electrical stimulation reduces DNA damage in chronic kidney failure patients: a randomized controlled trial," Biomarkers, vol. 23, Issue 5, 2018, pp. 1-11.

Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.

Scott Jeffrey, "How to Decalcify Your Pineal Gland (And Why It's Really Important for Higher Mental Performance)," (available at https://scottjeffrey.com/decalcify-your-pineal-gland/), Retrieved on May 23, 2019, 23 pages.

Seifi & Jeszri "Correlation of bone resorption induced by orthodontic tooth movement and expression of RANKL in rats", Dental Journal, vol. 26, No. 4 (2009).

Sethi et al. "Aortic stiffness: pathophysiology, clinical implications, and approach to treatment" Integr Blood Press Control. 2014; 7: 29-34.

Shahid et al., "Rhinosinusitis in Children," ISRN Otolaryngology, vol. 2012, Article ID 851831, (Dec. 2012), 11 pages.

Sharon M Moe, "Klotho: A Master Regulator of Cardiovascular Disease?," Circulation, vol. 125, (2012), pp. 2181-2183.

Shirtliff et al., "Assessment of the Ability of the Bioelectric Effect to Eliminate Mixed-Species Biofilms," Applied and Environmental Microbiology, vol. 71, (2005), pp. 6379-6382.

(56) References Cited

OTHER PUBLICATIONS

Shoji-Matsunaga et al. "Osteocyte regulation of orthodontic force-mediated tooth movement via RANKL expression." Scientific Reports, 7: 8753, published online Aug. 18, 2017, DOI:10.1038/s41598-017-09326-7.
Signature Orthodontics "Accelerated Tooth Movement", http://www.sigortho.com/accelerated-tooth-movement, visited Mar. 15, 2017.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative *Staphylococci* on Activities of Various Antimicrobial Agents," Antimicrobial Agents and Chemotherapy, vol. 42, (Apr. 1998), pp. 939-941.
Spadari et al., Electrical stimulation enhances tissue reorganization during orthodontic tooth movement in rats; Clinical Oral Investigations, Jan. 2017, vol. 21, Issue 1, pp. 111-120, Abstract.
Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.
Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.
Stenn et al., "Bioengineering the Hair Follicle," Organogenesis, 3(1): 6-13 (Jan.-Mar. 2007).
Stewart et al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.
Stoodley et al., "Influence of Electric Fields and pH on Biofilm Structure as Related to the Bioelectric Effect," Antimicrobial Agents and Chemotherapy, vol. 41, (1997), pp. 1876-1879.
Sultana et al., "Electrochemical Biofilm Control: A Review," Biofouling, vol. 31, (2015), pp. 745-758.
Szkotak et al., "Differential Gene Expression to Investigate the Effects of Low-Level Electrochemical Currents on Bacillus subtilis," AMB Express, vol. 1, (Nov. 2011), 12 pages.
Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009.07.115. Epub Jul. 28, 2009.
Tamaki et al., "Cardiomyocyte Formation by Skeletal Muscle-Derived Multi-Myogenic Stem Cells after Transplantation into Infarcted Myocardium", PLoS One 3(3): e1789. doi:10.1371/journal.pone.0001789 (Mar. 2008).
Tan et al., "Acupuncture Therapy for Essential Hypertension: a Network Meta-Analysis," Annals of Translational Medicine, vol. 7, (2019), pp. 1-12.
Tavlasoglu et al. "Is partial decalcification of posterior mitral annular bed logical in all mitral valve replacement procedures?" European Journal of Cardio-Thoracic Surgery 43 (2013) 449-450.
Thattaliyath et al., "Modified Skeletal Myoblast Therapy For Cardiac Failure Using AAV SDF1", Proc. Inti. Soc. Mag. Reson. Med. 16, p. 579 (2008).
Totsugawa, et al. "Ultrasonic annular debridement in minimally invasive aortic valve replacement" Gen Thorac Cardiovasc Surg. Jan. 2020;68(1):81-83. doi: 10.1007/s11748-019-01158-8. Epub Jun. 15, 2019. (Abstract Only).
Trafton, Anne, "A Noninvasive Method for Deep Brain Stimulation," MIT News Office, (available at http://news.mit.edu/2017/noninvasive-method-deep-brain-stimulation-0601), (Jun. 1, 2017), 3 pages.
Ucirvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.

Valvublator Heart Valve Regeneration, accessed Apr. 24, 2020 https://valvublator.com (6 pages).
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Vinod Krishnan, Ze'ev Davidovitch (eds.), Biological Mechanisms of Tooth Movement, (John Wiley & Sons 2015 (10 Pages).
W. Hoffmann, "Regeneration of the gastric mucosa and its glands from stem cells", Curr Med Chem, 15(29):3133-44 (2008).
Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.
Walsh & Choi "Biology of the RANK* RAN* OPG System in Immunity, Bone, and Beyond", Front Immunol. 2014; 5: 511.
Wang et al., "Controlling *Streptococcus* Mutans and *Staphylococcus aureus* Biofilms With Direct Current and Chlorhexidine," AMB Express, vol. 7, (Nov. 2017), 9 pages.
Warner"Inflammation Adds to Blood Pressure Risks, High Blood Pressure and C-Reactive Protein May Trigger Heart Attack, Stroke" Art. WebMD Health News (2003) 2 pages.
Wei et al., "Epicardial FSTL1 reconstitution regenerates the adult mammalian heart," Nature 525: 479-485 (Sep. 24, 2015).
Welch "RGS2 Proteins Regulate Blood Pressure" JASN Nov. 2010, 21 (11) 1809-1810.
Wellman et al., "Bacterial Biofilms and the Bioelectric Effect," Antimicrobial Agents and Chemotherapy, vol. 40, (1996), pp. 2012-2014.
What Is Elastin? http://www.keracyte.com/index.php/site/page?view=whatIsElastin.
Wong et al., "Dual Functional Polyelectrolyte Multilayer Coatings for Implants: Permanent Microbicidal Base With Controlled Release of Therapeutic Agents," Journal of the American Chemical Society, vol. 132, (2010), pp. 17840-17848.
Wu et al., "Vascular Calcification: an Update on Mechanisms and Challenges in Treatment," Calcified Tissue International, vol. 93, (Oct. 2013), pp. 365-373.
Fatemi et al. "Imaging elastic properties of biological tissues by low-frequency harmonic vibration" Proceedings of the IEEE, 91(10):1503-1519 (Oct. 2003).
FDA Approves Algovita Spinal Cord Stimulation System from Greatbatch, http://www.odtmag.com/contents/view_breaking-news/2015-12-02/fda-approves-algovita-spinal-cord-stimulation-system-from-greatbatch (Dec. 2, 2015).
Flachskampf et al., "Randomized Trial of Acupuncture to Lower Blood Pressure," Circulation, vol. 115, (2007), pp. 3121-3129.
Froughreyhani et al., "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.
Fukuoka et al. "Hair Regeneration Treatment Using Adipose-Derived Stem Cell Conditioned Medium: Follow-up With Trichograms" Eplasty, 15:e10 (Mar. 2015).
Fukuoka et al., "The Latest Advance in Hair Regeneration Therapy Using Proteins Secreted by Adipose-Derived Stem Cells" The American Journal of Cosmetic Surgery, 29(4):273-282 (2012).
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26(4):671-80.
Giladi et al., "Microbial Growth Inhibition by Alternating Electric Fields," Antimicrobial Agents and Chemotherapy, vol. 52, (2008), pp. 3517-3522.
Golberg et al., "Eradication of Multidrug-Resistant A. Baumannii in Burn Wounds by Antiseptic Pulsed Electric Field," Technology, vol. 2, (2014), pp. 153-160.
Golberg et al., "Pulsed Electric Fields For Burn Wound Disinfection in a Murine Model," Journal of Burn Care & Research, vol. 36, (2015), pp. 7-13.

(56) References Cited

OTHER PUBLICATIONS

Grad, D., "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).
Greenwald "Pulse pressure and arterial elasticity" QJM: An International Journal of Medicine, vol. 95, Issue 2, 2002, pp. 107-112.
Guimarães-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.
Hair Growth Factors, Nanogen, http://www.svijet-kose.com/dokumenti/Serum-vegf.pdf.
Hamman, R. "Modulation Of RANKL and Osteoprotegerin in Adolescents Using Orthodontic Forces", Masters Thesis, University of Tennessee (2010).
Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.
Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.
Hart, K. "RANKL and Osteoprotegerin Levels in Response to Orthodontic Forces" (2012). Theses and Dissertations (ETD). Paper 107. http://dx.doi.org/10.21007/etd.cghs.2012.0127.
HealthCMI, "Acupuncture Combats Hypertension In University of California Research," Available online at < https://www.healthcmi.com/Acupuncture-Continuing-Education-News/1688-acupuncture-c . . . >, (2016), 9 pages.
HealthCMI, "Acupuncture Controls Hypertension In Groundbreaking Trial," Available online at < https://www.healthcmi.com/Acupuncture-Continuing-Education-News/1804-acupuncture-c . . . >, (2017), 9 pages.
Healthcmi, "UC Irvine—Acupuncture Reduces Hypertension Confirmed," Available Online at < https://www.healthcmi.com/Acupuncture-Continuing-Education-News/1792-uc-irvine-acup . . . >, (2017), 6 pages.
Heart Valve Calcifications-Focused Ultrasound TherapyFocused Ultrasound Therapy; Research Paper Last Updated: Jan. 28, 2020, The Focused Ultrasound Foundation Newsletter (5 pages).
Hearts build new muscle with this simple protein patch, jacobsschool.ucsd.edu/news/news_releases/release.sfe?id=1813 (Sep. 16, 2015).
HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Holding et al. "The correlation of RANK, RANKL and TNFa expression with bone loss volume and polyethylene wear debris around hip implants" Biomaterials 27(30):5212-9—Nov. 2006.
Hopkins Medicine "Overview of Pacemakers and Implantable Cardioverter Defibrillators (ICDs)," hopkinsmedicine.org/healthlibrary/conditions/cardiovascular_diseases/ )verview of pacemakers and implantable cardioverter defibrillators icds 85,P00234/, last visited Sep. 12, 2018.
https://www.dicardiology.com/content/bioleonhardt-unveils-stem-pump Jan. 28, 2014.
Hu et al. "Klotho Deficiency Causes Vascular Calcification in Chronic Kidney Disease" J Am Soc Nephrol. Jan. 2011; 22(1): 124-136.
Hu Klein, "Vagus Nerve Stimulation: A new approach to reduce heart failure" Cardiology Journal (2010).
Huang et al. "Myocardial transfection of hypoxia-inducible factor-1a and co-transplantation of mesenchymal stem cells enhance cardiac repair in rats with experimental myocardial infarction", Stem Cell Research & Therapy 5:22 (2014) DOI: 10.1186/scrt410.
Hy et al., "Insulin-like growth factor 1 and hair growth," Dermatol Online J,; 5(2):1 (Nov. 1999).
Interesting study about prolactin, VEGF and angiogenic inhibition, http://www.regrowth.com/hair-loss-forums/topic/interesting-study-about-prolactin-vegf-and-angiogenic-inhibition/ (Nov. 2006).
International Search Report for International Application No. PCT/US19/52288, dated Jan. 10, 2020, 11 pages.
International Written Opinion for International Application No. PCT/US19/52288, dated Jan. 10, 2020, 07 pages.
Involvement of hepatocyte growth factor/scatter factor and Met receptor signaling in hair follicle morphogenesis and cycling, FASEB J Feb. 2000 14:319-332.
Israeli innovation uses nerve stimulation to treat heart failure https://www.israel21c.org/israeli-innovation-uses-nerve-stimulation-to-treat-heart-failure/ (Feb. 11, 2007).
Istanbullu et al., "Electrochemical Biofilm Control: Mechanism of Action," Biofouling, vol. 28, (2012), pp. 769-778.
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Jia et al., "Activin B Promotes Initiation and Development of Hair Follicles in Mice" Cells Tissues Organs, 198:318-326 (Feb. 2014).
Kanno et al., Establishment of a Simple and Practical Procedure Applicable to Therapeutic Angiogenesis, Circulation, 1999, pp. 2682-2687, vol. 99.
Kanzaki et al. "Local OPG gene transfer to periodontal tissue inhibits orthodontic tooth movement." J Dent Res 2004;83:92/ 925.
Kanzaki et al. "Local RANKL gene transfer to the periodontal tissue accelerates orthodontic tooth movement", Gene Therapy, (2006) 13, 678-685.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.
Kasimanickam et al., "Prevention and Treatment of Biofilms by Hybrid- and Nanotechnologies," International journal of Nanomedicine, vol. 8, (2013), pp. 2809-2819.
Kaur et al. "Electrically conductive polymers and composites for biomedical applications", RSC Adv., 2015,5, 37553-37567 DOI: 10.1039/C5RA01851J.
Keles et al. "Inhibition of tooth movement by osteoprotegerin vs. pamidronate under conditions of constant orthodontic force", Eur J Oral Sci. Apr. 2007;115(2):131-6.
Khan et al. "Accelerating Tooth Movement: What Options We Have?" J Dent Health Oral Disord Ther 2016, 5(7): 00181.
Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.
Kim et al., "Effect of Electrical Energy on the Efficacy of Biofilm Treatment Using the Bioelectric Effect," NPJ Biofilms and Microbiomes, vol. 1, (2015), Article 15016, 8 pages.
Kim et al., The effects of electrical current from a micro-electrical device on tooth movement, http://e-kjo.org/search.php?where=aview&id=10.4041/kjod.2008.38.5.337& . . . visited Aug. 2, 2017.
Bre et al. "Prevention of bioprosthetic heart valve calcification: strategies and outcomes". Curr Med Chem. 2014;21(22):2553-64. doi: 10.2174/0929867321666131212151216. PMID: 24358975.
Dalton et al. "New Insights into the Mechanism of Action of Soluble Klotho." Frontiers in endocrinology vol. 8 323. Nov. 17, 2017, doi: 10.3389/fendo.2017.00323.
Fu et al. "Loss of Klotho in CKD Breaks One's Heart" J Am Soc Nephrol Oct. 2015, 26 (10) 2305-2307; DOI: https://doi.org/10.1681/ASN.2015020200.
Lei "Mechanisms and Reversal Of Elastin Specific Medial Arterial Calcification." (2014). All Dissertations. 1307; tigerprints.clemson.edu/all_dissertations/1307/.
Lim et al. "a-Klotho Expression in Human Tissues." The Journal Of Clinical Endocrinology And Metabolism vol. 100,10 (2015): E1308-18. doi:10.1210/jc.2015-1800.
Lu et al. "Klotho/FGF23 Axis in Chronic Kidney Disease and Cardiovascular Disease" Kidney Dis (Jul. 2017) 3: 15-23; doi.org/10.1159/000452880.
Martín-Nuñez et al. "Implications of Klotho in vascular health and disease" World J Cardiol. Dec. 26, 2014; 6(12): 1262-1269.

(56) References Cited

OTHER PUBLICATIONS

Nowak et al. "Prognostic Value and Link to Atrial Fibrillation of Soluble Klotho and FGF23 in Hemodialysis Patients" PLoS One. Jul. 3, 2014;9(7):e100688. doi: 10.1371/journal.pone.0100688.
The et al. "Mechanistic Roles of Matrilin-2 and Klotho in Modulating the Inflammatory Activity of Human Aortic Valve Cells" Cells 2020, 9, 385; doi:10.3390/cells9020385.
Liebano et al. "Vascular Endothelial Growth Factor Release Following Electrical Stimulation in Human Subjects" Advances in Wound Care, vol. 3, No. 2, pp. 98-103 (Jun. 2013).
Morimoto et al. "Electrical Stimulation Enhances Migratory Ability of Transplanted Bone Marrow Stromal Cells in a Rodent Ischemic Stroke Model" Cell Physiol Biochem (Dec. 2018) 46:57-68.
Spadaccio et al. "In Situ Electrostimulation Drives a Regenerative Shift in the Zone of Infarcted Myocardium" Cell Transplantation, vol. 21, pp. 493-503, 2013 (Final Acceptance Mar. 2012).
King et al. "Mechanical Decalcification of the Aortic Valve" 272 The Annals of Thoracic Surgery vol. 42 No Sep. 3, 1986 (pp. 269-272).
Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.
Kose et al. "Citric acid as a decalcifying agent for the excised calcified human heart valves" Anadolu Kardiyol Derg 2008; 8: 94-8 (Eng Abstract).
Krishnan et al. (eds.), "Biological Mechanisms of Tooth Movement", John Wiley & Sons 2015 (10 pages).
Lasserre et al., "Influence of Low Direct Electric Currents and Chlorhexidine Upon Human Dental Biofilms," Clinical and Experimental Dental Research, vol. 2, (Jul. 2016), pp. 146-154.
Lasserre et al., "Oral Microbes, Biofilms and Their Role in Periodontal and Peri-Implant Diseases," Materials, vol. 11, (Sep. 2018), Article 1802, 17 pages.
Lee et al. "Hepatocyte growth factor (HGF) activator expressed in hair follicles is involved in in vitro HGF-dependent hair follicle elongation," J. Dermatol. Sci., 25(2):156-63 (Feb. 2001).
Lee et al., "Targeted Release of Tobramycin From a pH-Responsive Grafted Bilayer Challenged With *S. aureus*," Biomacromolecules, vol. 16, (2015), pp. 650-659.
Lei et al., "Efficacy of Reversal of Aortic Calcification by Chelating Agents," Calcified Tissue International, vol. 93, (Nov. 2013), 15 pages.
Leibrock et al., "NH4CI Treatment Prevents Tissue Calcification in Klotho Deficiency," Journal of the American Society of Nephrology, vol. 26, (2015), pp. 2423-2433.
Leonhardt "Micro Stimulator" http://www.bioleonhardt.com/microstimulator/.
Leonhardt "Leonhardt Adds HIF-1 Alpha To Estate of Bioelectric Controlled Release Regenerative Proteins" Press Release, Published Jun. 13, 2017.
Leonhardt, H.—Leonhardt Announces Vibrational Energy Device For Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.
Leonhardt's Launchpads Announces Filing of Patent for Bioelectric Stimulation Controlled Klotho Expression—Powerful Anti-aging and Regeneration Promoting Protein, by API Podder, Published: Mar. 13, 2019, available online at < https://mysocialgoodnews.com/leonhardts-launchpads-announces-filing-of-patent-for-bioelectric-stimulation-controlled-klotho-expression-powerful-anti-aging-and-regeneration-promoting-protein/.
Li "Regulation of Renal Oxygenation and Blood Pressure" Art. Virginia Commonwealth University, Richmond, VA, United States (Abstract).
Li et al., "Exogenous IGF-1 promotes hair growth by stimulating cell proliferation and down regulating TGF-(Beta) 1 in C57BL/6 mice in vivo" Growth Hormone & IGF Research, vol. 24, Issues 2-3, pp. 89-94 (Apr.-Jun. 2014).
Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Li et al., "The Mechanism of Acupuncture in Treating Essential Hypertension: A Narrative Review," International Journal of Hypertension, vol. 2019, (2019), Article ID 8676490, 10 pages.
Li, et al. "Local injection of RANKL facilitates tooth movement and alveolar bone remodelling." Oral Diseases, 25(2), 550-560. https://doi.org/10.1111/odi.13013.
Longhurst et al. "Evidence-based blood pressure reducing actions of electroacupuncture: mechanisms and clinical application" Sheng Li Xue Bao. Oct. 25, 2017; 69(5): 587-597.
Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.
Mass Device "Greatbatch wins FDA PMA for Algovita SCS" http://www.massdevice.com/greatbatch-wins-fda-pma-for-algovita-scs/ (Dec. 1, 2015).
McBride et al. "Aortic valve decalcification" J Thorac Cardiovasc Surg. Jul. 1990; 100(1):36-42; discussion 42-3 (Abstract Only).
McLean et al., "Training the Biofilm Generation—a Tribute to J. W. Costerton," Journal of Bacteriology, vol. 194, (Dec. 2012), pp. 6706-6711.
Medtronic "Cardiac Resynchronization Therapy (CRT) Devices For Heart Failure" http://www.medtronic.com/us-en/patients/treatments-therapies/crt-devices.html.
Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).
Mosteiro et al. "Tissue damage and senescence provide critical signals for cellular reprogramming in vivo." Science, 2016; 354 (6315): aaf4445 DOI: 10.1126/science.aaf4445.
Niiranen et al., "Relative Contributions of Arterial Stiffness and Hypertension to Cardiovascular Disease: The Framingham Heart Study," Journal of the American Heart Association, vol. 5, No. 11, 2016, 8 pages.
Nimeri et al. "Acceleration of tooth movement during orthodontic treatment—a frontier in Orthodontics", Prog Orthod 2013; 14:42; DOI: 10.1186/2196-1042-14-42.
Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.
Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.
Nordstrom "Electrical Stimulation Blood Pressure Treatment Devices Market to Set Astonishing Growth by 2026" Art. Apr. 4, 2019 Gator Ledger.
Novickij et al., "Induction of Different Sensitization Patterns of MRSA to Antibiotics Using Electroporation," Molecules, vol. 23,(2018), Article 1799, 10 pages.
O'Neill et al., "Recent Progress in the Treatment of Vascular Calcification," Kidney International, vol. 78, (Dec. 2010), pp. 1232-1239.
Otero et al. "Expression and Presence of OPG and RANKL mRNA and Protein in Human Periodontal Ligament with Orthodontic Force", Gene-Regulation-and-Systems-Biology, 2016, 10, 15-20.
Our Approach to Improve Hair Loss by Increasing Hair Growth Factor IGF-1, http://www.jhgc.com.sg/theory/igf-1/index.html.

(56) References Cited

OTHER PUBLICATIONS

Palza et al., "Electroactive Smart Polymers for Biomedical Applications," Materials, vol. 12, (2019), 24 pages.
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
Park, Alice "Shrinking Stem Cells Are the Real Reason for Hair Loss" Time, (Feb. 5, 2016).
Pierce et al. "Collection and characterization of amniotic fluid from scheduled C-section deliveries," Cell Tissue Bank, DOI 10.1007/s10561-016-9572-7 (Springer, 2012) and is available from Irvine Scientific.
Plumbing Today, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.
Pozo et al., "Bioelectric Effect and Bacterial Biofilms. A Systematic Review," The International Journal of Artificial Organs, vol. 31, (2008), pp. 786-795.
Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35-40.
Pozo et al., "Prevention of *Staphylococcus epidermidis* Biofilm Formation Using Electrical Current," Journal of Applied Biomaterials & Functional Materials, vol. 12, (2014), pp. 81-83.
Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.
Price et al. "Mitral Valve Repair is Feasible Following Extensive Decalcification and Reconstruction of the Atrioventricular Groove" J Heart Valve Dis. Jan. 2015;24(1):46-52 (Abstract Only).
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.
Silva et al., "Analgesia Induced by 2- or 100-Hz Electroacupuncture in the Rat Tail-Flick Test Depends on the Activation of Different Descending Pain Inhibitory Mechanisms", The Journal of Pain, vol. 12, No. 1, Jan. 2011. (Year: 2011).

* cited by examiner

METHODS, SYSTEMS, AND DEVICES FOR HEART VALVE DECALCIFICATION, REGENERATION, AND REPAIR

CROSS-REFERENCE TO RELATED APPLICATIONS

This application is a continuation-in-part of U.S. Ser. No. 15/812,760, filed on Nov. 14, 2017 (US 2018/0064935A1, Mar. 8, 2018, now U.S. Pat. No. 10,960,206, issued on Mar. 30, 2021), which is a continuation-in-part of U.S. Ser. No. 15/460,129, filed on Mar. 15, 2017 (US 2017/0266371A1, Sep. 21, 2017, now U.S. Pat. No. 10,646,644, issued on May 12, 2020), which claims the benefit under 35 USC § 119 of:

U.S. Provisional Patent Application Ser. No. 62/308,702, filed Mar. 15, 2016;

U.S. Provisional Patent Application Ser. No. 62/363,012, filed Jul. 15, 2016;

U.S. Provisional Patent Application Ser. No. 62/364,472, filed Jul. 20, 2016;

U.S. Provisional Patent Application Ser. No. 62/375,271, filed Aug. 15, 2016;

U.S. Provisional Patent Application Ser. No. 62/385,124, filed Sep. 8, 2016;

U.S. Provisional Patent Application Ser. No. 62/454,521, filed Feb. 3, 2017; and U.S. Provisional Patent Application Ser. No. 62/352,930, filed Jun. 21, 2016.

This application additionally claims the benefit under 35 U.S.C. § 119 of U.S. Provisional Patent Application Ser. No. 62/831,083, pending, filed Apr. 8, 2019, the disclosure of each of which is hereby incorporated herein in its entirety by this reference.

TECHNICAL FIELD

Embodiments of this disclosure relate generally to methods, systems, and devices for heart valve decalcification, regeneration, and repair. In particular, embodiments of this disclosure relate to methods, systems, and devices employing mechanical and/or chemical removal of calcification from a heart valve and optionally regenerating and/or repairing the heart valve after the removal of calcification therefrom.

BACKGROUND

Calcification deposits on the heart valves cause challenges for proper and competent heart valve function. Although the cardiac muscle may be strong and operative, improper valve function can lead to serious complications, including heart failure, blood clotting, stroke, heart attack, arrhythmia, etc. About one quarter of all Americans suffer hardening valves by the age of 65, and about half by the age of 85. The only treatment is surgical replacement.

Various methods have been proposed for improvement of heart function, which can be either surgical or percutaneous, as mentioned in U.S. Pat. No. 5,957,949 to Howard J. Leonhardt et al. issued on Sep. 28, 1999, and U.S. Patent Publication No. 20050171578 to Howard J. Leonhardt published on Aug. 4, 2005, the disclosure of each of which is hereby incorporated herein in its entirety by this reference.

Procedures and devices exist to facilitate the removal of calcified heart valves and the implantation of replacement valves. However, these procedures have many drawbacks, such as requiring patients to take blood thinners for the rest of their life.

BRIEF SUMMARY

Some embodiments of the present disclosure may include methods of heart valve decalcification. The methods may include mechanically removing calcium deposits on a heart valve, and removing debris from the mechanical decalcification via suction. The mechanical removal of the calcium deposits may be accomplished with a burr and/or an ultrasonic device. In some embodiments, mechanical removal of the calcium deposits may be accomplished with a handheld mechanical decalcification device comprising a bur extending from a hand piece.

In some embodiments, calcium deposits on the heart valve may be further removed by directing a stream of biocompatible solvent onto the heart valve. After cleaning, bioelectric stimulation may be provided to the heart valve. Additionally, the heart valve may be bathed with a biochemical bath to encourage healing and regeneration of tissue.

Optionally, the shape of the valve may be reformed by installing a nitinol ring and, if needed, autologous cell created heart valve leaflets can be placed.

Another embodiment of the present disclosure may include a catheter system for removing plaque deposits from a heart valve. The catheter system may include at least one mechanical decalcification device configured for cleaning the edges of heart valve leaflets, and at least one active aspiration device. The at least one mechanical decalcification device may comprises a bur and/or an ultrasonic device. The system may additionally include a deployable net apparatus configured to encompass at least a portion of a heart valve.

In some embodiments, the system may include a biocompatible solvent delivery device configured for delivering a stream of biocompatible solvent to a heart valve. The system may also include a bioelectric signal array configured to deliver bioelectric stimulation to the heart valve, and/or a micro infusion pump configured to deliver a regeneration cocktail composition to the heart valve. An optical viewing system may be included in the system, and the system may include at least one cerebral protection device.

BRIEF DESCRIPTION OF THE DRAWINGS

While this disclosure concludes with claims particularly pointing out and distinctly claiming specific embodiments, various features and advantages of embodiments within the scope of this disclosure may be more readily ascertained from the following description when read in conjunction with the accompanying drawings, in which:

DETAILED DESCRIPTION

Figure 1:
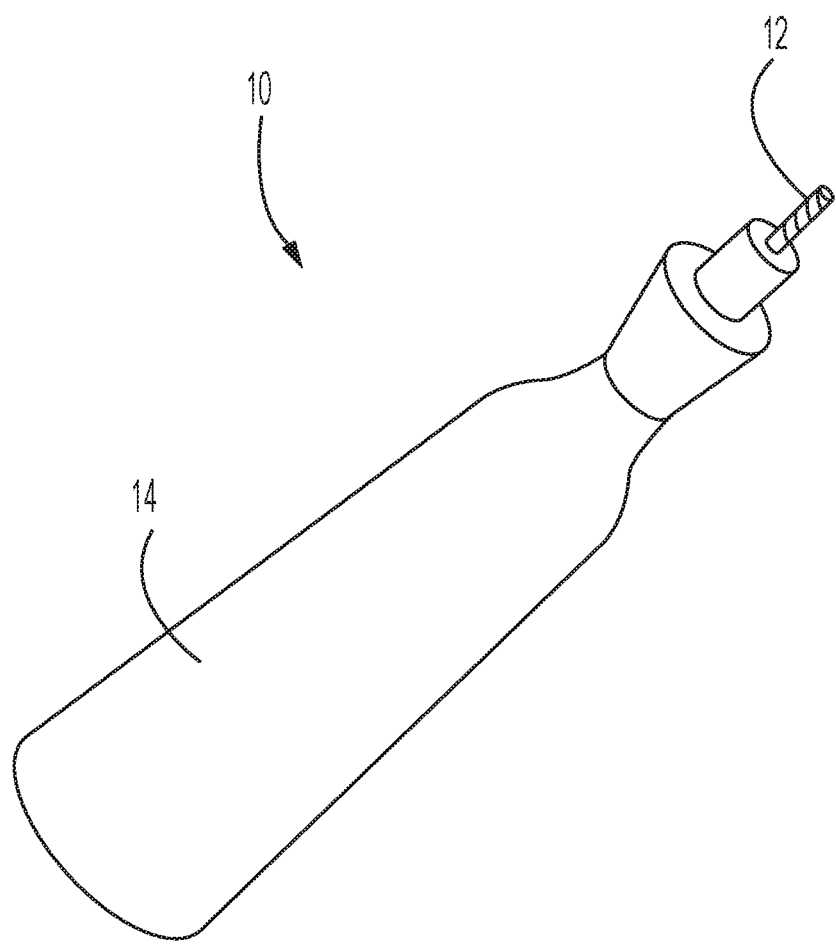
FIG. 1 illustrates a handheld mechanical decalcification device according to an embodiment of the present disclosure.

In the following detailed description, reference is made to the accompanying drawings, which form a part hereof, and in which are shown, by way of illustration, specific examples of embodiments in which the present disclosure may be practiced. These embodiments are described in sufficient detail to enable a person of ordinary skill in the art to practice the present disclosure. However, other embodiments may be utilized, and structural, system, and process changes may be made without departing from the scope of the disclosure.

The following description may include examples to help enable one of ordinary skill in the art to practice the disclosed embodiments. The use of the terms "exemplary," "by example," and "for example," means that the related description is explanatory, and though the scope of the disclosure is intended to encompass the examples and legal equivalents, the use of such terms is not intended to limit the scope of an embodiment or this disclosure to the specified components, steps, features, functions, or the like.

Furthermore, specific implementations shown and described are only examples and should not be construed as the only way to implement the present disclosure unless specified otherwise herein. It will be readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

As used in this specification, the terms "substantially," "about," and "approximately" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, at least about 99% met, or even 100% met.

The phrase "at least one of" when used with a list of items means different combinations of one or more of the listed items may be used and only one of each item in the list may be needed. For example, "at least one of item A, item B, and item C" may include, without limitation, item A or item A and item B. This example may also include item A, item B, and item C, or item B and item C. In other examples, "at least one of" may be, without limitation, two of item A, one of item B, and 10 of item C; four of item B and seven of item C; and other suitable combinations.

As used in this disclosure, any relational term, such as "first," "second," "over," "top," "bottom," "side," etc., is used for clarity and convenience in understanding the disclosure and accompanying drawings and does not connote or depend on any specific preference, orientation, or order, except where the context clearly indicates otherwise.

As used in this disclosure, the term "and/or" means and includes any and all combinations of one or more of the associated listed items.

When one component is "associated" with another component, the association is a physical association in these examples. For example, a first component may be considered to be associated with a second component by being secured to the second component by welding, adhesives, fasteners or connected to the second component in some other suitable manner. The first component may also be connected to the second component using a third, intervening component by which the first component may also be considered to be associated with the second component.

The illustrations presented in this disclosure are not meant to be actual views of any particular system or device, but are merely idealized representations that are employed to describe the disclosed embodiments. Thus, the drawings are not necessarily to scale and relative dimensions may have been exaggerated for the sake of clarity. Additionally, elements common between figures may retain the same or similar numerical designation.

The following description provides specific details in order to provide a thorough description of embodiments of this disclosure. However, a person of ordinary skill in the art will understand that the embodiments of this disclosure may be practiced without employing these specific details.

Over time, heart valves may become dysfunctional from calcification build up, and clots may form, which may cause strokes. Additionally, heart valves lose shape, and thus function, and heart valve leaflets degenerate and do not function properly.

Embodiments of the present disclosure are designed to remove plaque (e.g., calcification) from a heart valve via processes involving one or more of the following steps: 1) a mechanical removal of calcified material, 2) a simultaneous removal of calcific material during decalcification, 3) an ultrasonic cleaning of the previously decalcified valve, 4) a chemical rinsing of the calcified region using a biocompatible solvent, such as a citric acid solution, and/or 5) an applied electric stimulation to up-regulate targeted gene expression via electroceutical therapy to encourage regeneration of the heart valve.

In some embodiments, such plaque removal and valve revitalization may be accomplished with one or more handheld surgical device, such as with open-heart surgery techniques for surgical valve repair. In further embodiments, such plaque removal and valve revitalization may be accomplished with one or more devices using percutaneous delivery (e.g., transcatheter), such as for transthoracic valve repair.

FIG. 1 shows an isometric view of a handheld mechanical decalcification device 10 for use in open surgery, according to an embodiment of the present disclosure. For example, the handheld mechanical decalcification device 10 may be utilized within an open-heart surgery, or as an alternative to a surgical aortic valve replacement (SAVR). The handheld mechanical decalcification device 10 may include a bur 12 extending from a hand piece 14. As shown in FIG. 1, and as shown in a magnified view of the bur 12 in FIG. 2, the bur may include a plurality of blades and flutes in a spiral configuration extending along the circumference of the bur.

Optionally, the bur may also include a rounded tip portion, which may prevent unintentional tissue damage during use. Other bur configurations may also be utilized. For example, an abrasive bur having a surface comprising abrasive material may be utilized, such as bur having a surface comprising diamond particles.

In use, a heart valve (not shown) may be exposed and calcified regions may be removed by mechanical decalcification. The decalcification may be administered through the handheld mechanical decalcification device 10 via the contact and movement of the surface of the bur 12 relative to the calcified regions. For example, the bur 12 may be rotated, vibrated, and/or reciprocated. Accordingly, the bur 12 may deliver sufficient mechanical stress to remove large regions of calcification.

Simultaneously, debris may be removed by way of a handheld, or largescale, suction device. Prior to and/or after the decalcification via the handheld mechanical decalcification device 10, ultrasonic cleaning may optionally be performed with an ultrasonic cleaning device. A brief ultrasonic pulse may be used post-decalcification to mechanically disperse any remaining calcium particles. Any released calcium micro-particles or other associated debris that escapes the surgeon's scrutiny and the calcium suction device may be small enough to be partially transported to regional lymph nodes. Ultrasound pulsation may be repeated until all particles are removed.

At the completion of mechanical decalcification, the heart valve may be further cleansed by applying a biocompatible solvent, such as a citric acid solution, to the regions where the calcification has been removed. For example, a syringe may filled with the biocompatible solvent and may be utilized to direct a stream of the biocompatible solvent onto the heart valve. The biocompatible solvent may be a non-harmful chemical that degrades calcified deposits, and may facilitate the removal of microparticles from the site and encourage healing and regeneration of tissue for complete recovery.

Once the heart valve has been cleaned of calcification deposits, electrodes to stimulate regeneration of the heart valve may apply electric stimulation of the heart valve. The electric stimulations of the heart valve, and optionally other tissue in the region of the heart valve, may provide one or more of various bioelectric signals to stimulate regeneration of the heart valve. For example, the electrodes may utilized to provide a bioelectric SDF-1 stem cell homing signal, a bioelectric IGF-1 DNA repair signal, a bioelectric HGF regeneration signal, a bioelectric EGF regeneration signal, a bioelectric Activin A+B regeneration signal, a bioelectric follistatin regeneration signal, a bioelectric Tropoelastin elasticity regeneration signal, a bioelectric eNOS blood flow signal, a bioelectric VEGF blood flow signal, a bioelectric stem cell proliferation signal, and/or a bioelectric stem cell differentiation control signal.

The heart valve may then be bathed with a biochemical bath to encourage healing and regeneration of tissue to facilitate complete recovery and full use of the heart valves. For example, the biochemical bath may comprise a cocktail of regenerative agents including any combination of the following: stem cells, endothelial progenitor cells, selected exosomes, selected alkaloids, selected anti-inflammatory agents, nutrient hydrogel, organ specific matrix, selected growth factors, amniotic fluid, placenta fluid, cord blood, and embryonic sourced growth factors and cells.

In certain embodiments, the device, system, and/or method is combined with bioelectric signaling for, e.g., the regeneration of heart tissue. Such bioelectric signaling generally modulates (e.g., upregulates) the expression of klotho, follistatin, EGF, HGF, tropoelastin and/or other regeneration promoting proteins. (See, e.g., the incorporated US 2018/0064935A1 to Leonhardt et al. and PCT International Application No. PCT/US2020/021556, filed Mar. 6, 2020, and also incorporated herein by this reference, for various appropriate bioelectric signals).

For instance, Klotho both prevents re-calcification and regenerates cardiac tissue. Klotho may be released into the blood stream simply by stimulating the subject's thigh muscle with the proper bioelectric signals for about 45 minutes, once or twice a month (e.g., at home) to prevent heart valve re-calcification. Such a treatment can be supplemented with, e.g., a once a year infusion of elastin nanoparticles (in a clinic). See, generally, Chen et al. "The Role and Mechanism of $\alpha$-Klotho in the Calcification of Rat Aortic Vascular Smooth Muscle Cells" *Biomed Res Int.* 2015; 2015: 194362; Hu et al. "Klotho Deficiency Causes Vascular Calcification in Chronic Kidney Disease" *J Am Soc Nephrol.* 2011 January; 22(1): 124-136; Chen et al. "Deficiency in the anti-aging gene Klotho promotes aortic valve fibrosis through AMPK$\alpha$-mediated activation of RUNX2" *Aging Cell.* 2016 October; 15(5): 853-860; and Chen et al. "Secreted Klotho Attenuates Inflammation-Associated Aortic Valve Fibrosis in Senescence-Accelerated Mice P1" *Hypertension* 2018; 71:877-885, the contents of the entirety of each of which are herein incorporated by this reference.

In further embodiments, such plaque removal and valve revitalization may be accomplished with one or more devices using percutaneous delivery (e.g., transcatheter), such as for transthoracic valve repair.

In some embodiments, methods of the present disclosure may be performed with a catheter system, such as shown in FIGS. 2-14. The catheter system may include components located at a distal end, the distal end configured for percutaneous insertion into a patient's body, and may include components located at a proximal end, the proximal end configured to remain outside of the patient's body and accessible to an operator of the catheter system, such as a surgeon.

The catheter system may be utilized for decalcifying and regenerating heart valves, so that a patient may keep their own heart valves instead of getting an implant. The catheter system may be utilized to perform three methods of decalcification. Additionally, the catheter system may be utilized to regenerate heart valve tissue.

In further embodiments, the catheter system may be utilized to implement shape reform via a nitinol ring, along with decalcification and regeneration.

Figure 2:
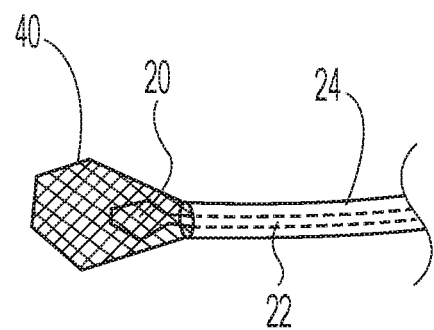
FIG. 2 illustrates a bur and deployable net apparatus at a distal end of a catheter system according to an embodiment of the present disclosure.
Figure 3:
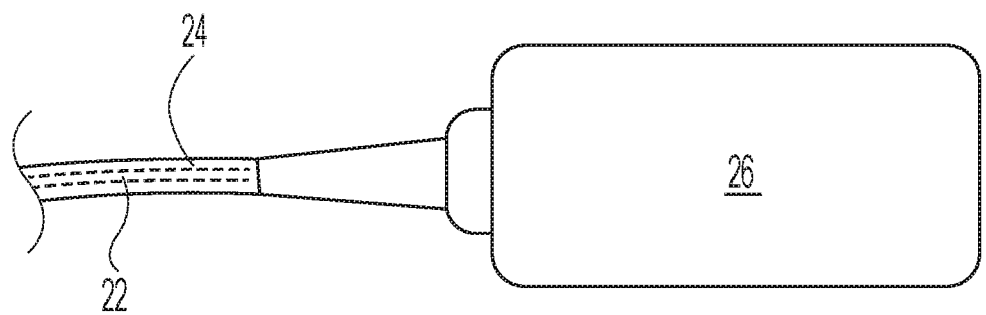
FIG. 3 illustrates a drive mechanism at a proximal end of the catheter system of FIG. 2.

For mechanical removal of calcium deposits, the catheter system may include multiple components, such as at least one mechanical decalcification device. As shown in FIG. 2, the catheter system may include a bur 20 located at the tip of the distal end, which may include an abrasive surface. The bur may have a generally frustoconical shaped tip and may be connected to a shaft 22 that is located within a lumen 24 of the catheter system. The shaft 22 may extend through the lumen 24 to a drive mechanism 26 located at the proximal end of the catheter system, as shown in FIG. 3.

The drive mechanism 26 may be configured to cause the bur 20 to move at the distal end of the catheter system to mechanically remove calcium deposits on the heart valve. In some embodiments, the drive mechanism 26 may comprise a motor configured to rotate the bur 20 via the shaft 22. In further embodiments, the drive mechanism 26 may comprise a vibration generator, such as an eccentric rotating mass vibration motor, configured to vibrate the bur 20 via the shaft 22. Accordingly, the drive mechanism 26 may be configured to cause the bur 20 to rotate, vibrate, reciprocate, and/or translate.

Figure 4:
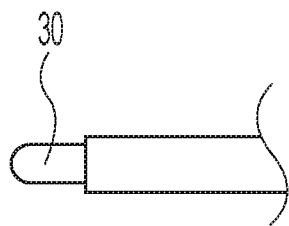
FIG. 4 illustrates an ultrasonic tip at a distal end of the catheter system of FIG. 2.
Figure 5:
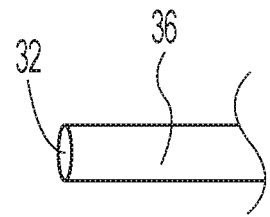
FIG. 5 illustrates an opening for the delivery of a biocompatible solvent at a distal end of the catheter system of FIG. 2.
Figure 6:
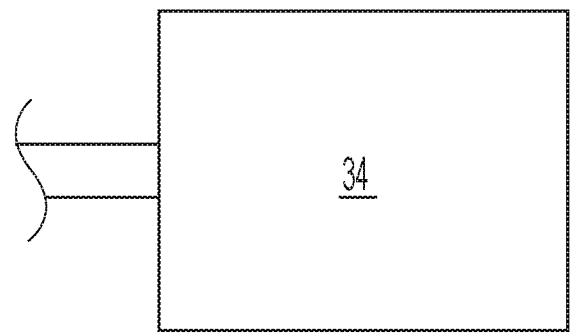
FIG. 6 illustrates an ultrasonic wave generator at a proximal end of the catheter system of FIG. 2.

For additional decalcification and cleaning, the catheter system may include an ultrasonic tip 30 located at the distal end, as shown in FIG. 4, and an opening 32 at the distal end for the delivery of the biocompatible solvent, as shown in FIG. 5. The ultrasonic tip 30 may be coupled to an ultrasonic wave generator 34 located at the proximal end, as shown in FIG. 6, configured to deliver ultrasonic waves to the ultrasonic tip 30.

Figure 7:
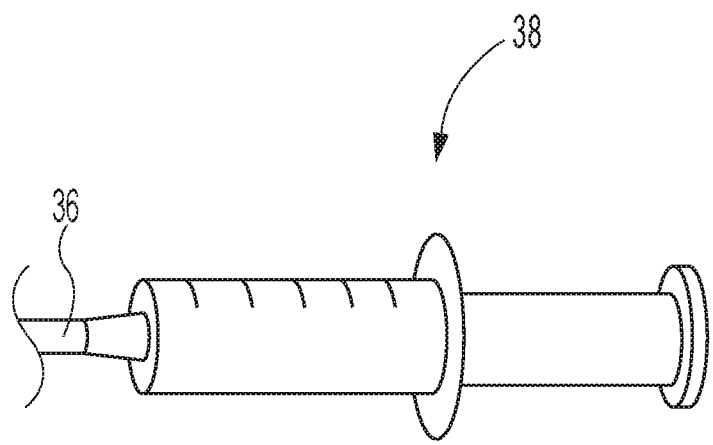
FIG. 7 illustrates a biocompatible solvent delivery device at a proximal end of the catheter system of FIG. 2.

A lumen 36 of the catheter system may extend from the opening 32 to a biocompatible solvent delivery device 38 located at the proximal end of the catheter system, as shown in FIG. 7, for directing the biocompatible solvent through the lumen 36 and out of the opening 32 at the distal end. For example, the biocompatible solvent delivery device 38 may be a syringe filled with the biocompatible solvent. Accordingly, pressurized biocompatible solvent may be directed through the lumen 36 and out of the opening 32 as a relatively high-pressure stream of biocompatible solvent.

As shown in FIG. 2, the catheter system may also include a deployable net apparatus 40 located at the distal end proximal to the bur 20. The deployable net apparatus 40 may be deployed to encompass at least a portion of a heart valve, or optionally the entire valve, during operation of the bur to facilitate the removal of the calcification dislodged from the heart valve in the process. The deployable net apparatus 40 may be comprised of electrospun polymers forming a nanoscale fiber mesh. Optionally, other devices may be implemented instead of, or in combination with, the net apparatus to hold the heart valve during cleaning, such as a suction cup (not shown).

The catheter system may include a deflecting tip-guiding catheter and an optical viewing catheter to facilitate the guiding of the catheter system components at the distal end of the catheter system during use.

Figure 8:
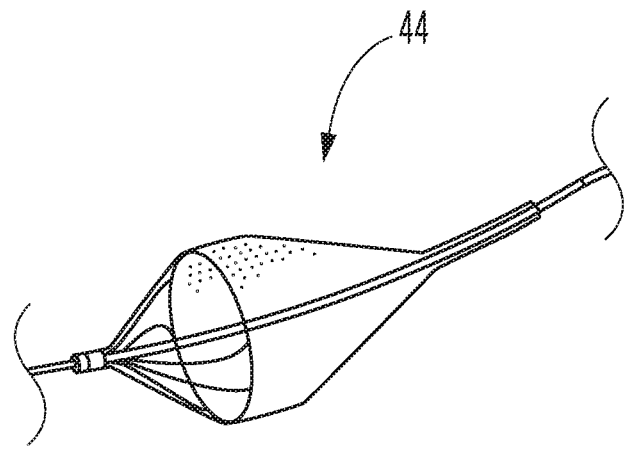
FIG. 8 illustrates a cerebral protection device at a distal end of the catheter system of FIG. 2.

The catheter system may also include additional components for the capture and removal of debris. For example, the catheter system may include one or more cerebral protection devices 44 (i.e., an embolic protection device), as shown in FIG. 8, located at a distal portion of the catheter system for the capture of debris.

Figure 9:
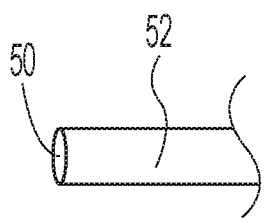
FIG. 9 illustrates an opening of an active aspiration system at a distal end of the catheter system of FIG. 2.
Figure 10:
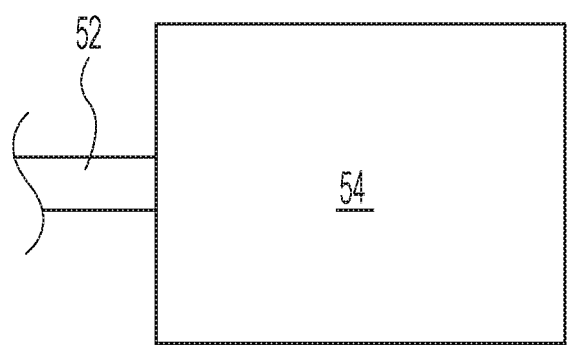
FIG. 10 illustrates an active aspiration device at a proximal end of the catheter system of FIG. 2.

The catheter system may additionally include an active aspiration system. The active aspiration system may comprise at least one opening 50 at the distal end of a lumen 52, as shown in FIG. 9, and an active aspiration device 54 may be coupled to the lumen 52 of the catheter system at the proximal end, as shown in FIG. 10, to facilitate the removal of debris through the lumen 52 from the at least one opening 50 via suction.

Figure 11:
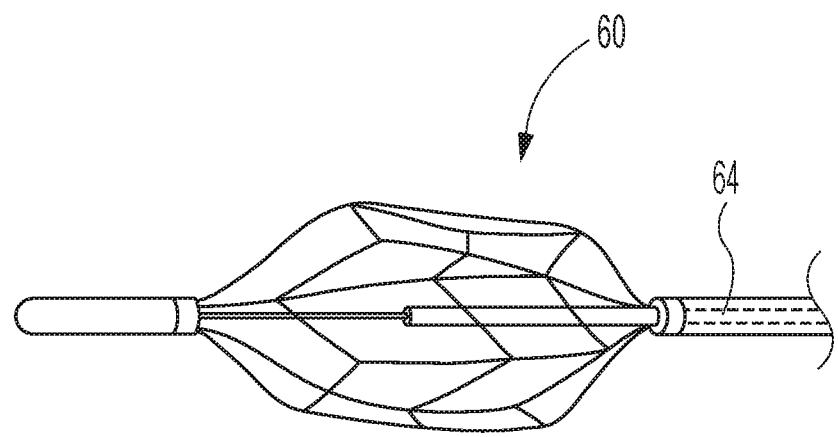
FIG. 11 illustrates a bioelectric signal array at a distal end of the catheter system of FIG. 2.
Figure 12:
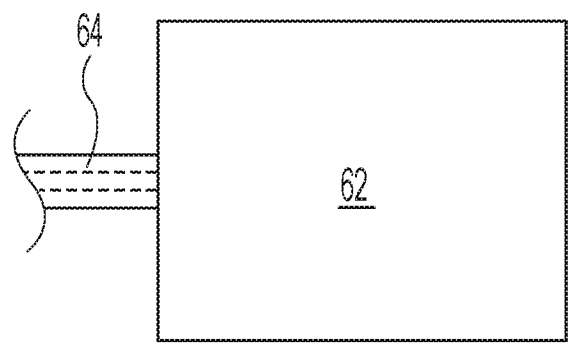
FIG. 12 illustrates a bioelectric signal generator at a proximal end of the catheter system of FIG. 2.

As shown in FIG. 11, a bioelectric signal array 60 may be located at the distal end of the catheter system for the delivery of the bioelectric stimulation to the heart valve after the cleaning of calcification deposits. A bioelectric stimulator signal generator 62 may be positioned at the proximal end of the catheter system, as shown in FIG. 12, and may be coupled to the bioelectric signal array via wires 64 to provide bioelectric signals to the bioelectric signal array 60.

Figure 13:
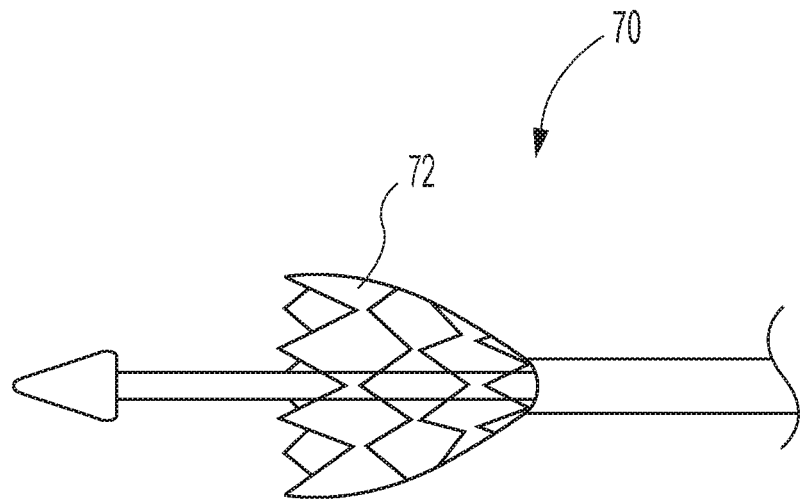
FIG. 13 illustrates a nitinol ring placement catheter at a distal end of the catheter system of FIG. 2.

Optionally, as shown in FIG. 13, the catheter system may include a nitinol ring placement catheter 70 for the placement of a nitinol ring 72 at the heart valve to reform the valve shape.

In some embodiments, the catheter system may include various catheters to implement various components of the catheter system. In further embodiments, multiple components of the catheter system may be incorporated into a single catheter. The use of multiple catheters may make the design of the catheter system simpler. Incorporating multiple components on a single catheter, however, may reduce the number of times that catheters are inserted and removed from a patient during a procedure. Accordingly, embodiments of the present disclosure contemplate any variety of combination of the various components on one or more catheters to provide the catheter system.

In one embodiment, every component of the catheter system may be incorporated into a single catheter. In another embodiment, the catheter system may be comprised of a plurality of catheters, each catheter of the plurality incorporating only a single component of the catheter system at each of the proximal and distal ends thereof. In yet further embodiments, the catheter system may include a plurality of catheters with at least one catheter of the plurality of catheters incorporating multiple components of the catheter system at each of its proximal and distal ends.

The catheter system is designed to be implemented through transvascular manipulation as a supplement to, or a replacement for, transcatheter aortic valve replacement (TAVR). TAVR procedures may provide a critically needed alternative therapy for patients with severe aortic stenosis.

Heart valve surgery is very costly and disrupts a patient's life. This minimally invasive surgery is designed to prevent heart surgery and return the valves to full optimal capacity with little downtime. As the baby boom generation begins to experience heart valve complications, embodiments of this disclosure may assist physicians to enhance the quality of life for each patient.

For the cleaning operation, the bur 20, the ultrasonic tip 30, and biologically safe solvent may be utilized, such as in a sequence, to fully decalcify and clean the heart valve leaflets and orifice of the heart valve. Concurrently, optical viewing systems may provide visualization of areas being cleaned. For example, the cleaning operation may be guided via standard fluoroscopic approaches, but may also be accompanied by IVUS imaging probes attached to the distal end of the catheter system. The net apparatus 40, and/or a suction cup system may hold the heart valve leaflets during cleaning. Additionally, during decalcification or subsequent procedures, the catheter system may be designed to expand the net apparatus 40 to facilitate the removal of any calcification dislodged from the heart valve in the process. Additionally, debris may be captured by one or more cerebral protection devices 44 and/or removed via suction.

After the cleaning operation, bioelectric regeneration signals may be provided to the heart valve by the bioelectric signal array 60 powered by the bioelectric stimulator signal generator 62 to regenerate the native heart valve by recruiting stem cells and building new healthy tissues. For example, the bioelectric signals may include one or more of a bioelectric SDF-1 stem cell homing signal, a bioelectric IGF-1 DNA repair signal, a bioelectric HGF regeneration signal, a bioelectric EGF regeneration signal, a bioelectric Activin A+B regeneration signal, a bioelectric follistatin regeneration signal, a bioelectric Tropoelastin elasticity regeneration signal, a bioelectric eNOS blood flow signal, a bioelectric VEGF blood flow signal, a bioelectric stem cell proliferation signal, and/or a bioelectric stem cell differentiation control signal.

Optionally, the nitinol ring 72 is placed by the nitinol ring placement catheter 70, such as if the above decalcification and regeneration procedure has not restored full function. Furthermore, autologous cell created heart valve leaflets may be placed via a heart valve catheter-based delivery system if the previous steps have not restored full function.

Figure 14:
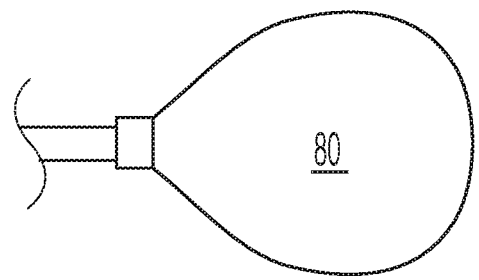
FIG. 14 illustrates a micro infusion pump at a proximal end of the catheter system of FIG. 2.

Additionally, such as if all of the above has failed, a micro infusion pump 80, as shown in FIG. 14, may be connected to a lumen of the catheter system and a component regeneration cocktail composition may be infused until function is restored. For example, the micro infusion pump 80 may be utilized to deliver a biochemical bath comprising a cocktail of regenerative agents including any combination of the following: stem cells, endothelial progenitor cells, selected exosomes, selected alkaloids, selected anti-inflammatory agents, nutrient hydrogel, organ specific matrix, selected growth factors, amniotic fluid, placenta fluid, cord blood, and embryonic sourced growth factors and cells.

Optionally, a robot could control the full procedure of cleaning, regeneration, nitinol ring 72 placement and percutaneous autologous cell created valve placement, or portions thereof.

The catheter system may be designed to be fed through femoral artery, radial artery or other access points into the heart chamber and specifically is associated with a heart valve.

The systems, devices, and methods herein may be utilized to decalcify the heart valves, restores shape, and regenerates them restoring full normal function.

The disclosed systems, devices, and methods may reduce calcification in a heart valve, and may regenerate the heart valve with stem cell recruitment and differentiation supported by a full range of regeneration promotion proteins. The disclosed systems, devices, and methods may be combined with a non-surgical reforming option when required or thought desirable.

Alternative embodiments and variations in the detail design of the disclosed systems and devices are contemplated within the scope of the invention.

While certain illustrative embodiments have been described in connection with the figures, those of ordinary skill in the art will recognize and appreciate that the scope of this disclosure is not limited to those embodiments explicitly shown and described in this disclosure. Rather, many additions, deletions, and modifications to the embodiments described in this disclosure may be made to produce embodiments within the scope of this disclosure, such as those specifically claimed, including legal equivalents. In addition, features from one disclosed embodiment may be combined with features of another disclosed embodiment while still being within the scope of this disclosure, as contemplated by the inventor.

REFERENCES (The contents of the entirety of each of which is incorporated herein by this reference.)

Dahm M. et al. "Decalcification of the aortic valve does not prevent early recalcification" J Heart Valve Dis., 9(1):21-6. (January 2008).

Chen et al. "The Role and Mechanism of α-Klotho in the Calcification of Rat Aortic Vascular Smooth Muscle Cells" Biomed Res Int. 2015; 2015: 194362.

Hu et al. "Klotho Deficiency Causes Vascular Calcification in Chronic Kidney Disease" *J Am Soc Nephrol.* 2011 January; 22(1): 124-136.

Chen et al. "Deficiency in the anti-aging gene Klotho promotes aortic valve fibrosis through AMPKα-mediated activation of RUNX2" Aging Cell. 2016 October; 15(5): 853-860.

Chen et al. "Secreted Klotho Attenuates Inflammation-Associated Aortic Valve Fibrosis in Senescence-Accelerated Mice P1" *Hypertension* 2018; 71:877-885.

Kose N. et al., "Citric acid as a decalcifying agent for the excised calcified human heart valves" Anadolu Kardiyol Derg., 2008 April; 8(2):94-8.

"Focused Ultrasound Therapy" https://fusfoundation.org/diseases-and-conditions/cardiovascular/heart-valve-calcifications (28 Jan. 2020).

What is claimed is:

1. A catheter system for removing plaque deposits from a heart valve of a patient, the system comprising:
   at least one mechanical decalcification device configured for cleaning the edges of heart valve leaflets,
   a bioelectric signal generator, and
   a bioelectric signal array associated with the system and the bioelectric signal generator, wherein the bioelectric signal array is configured to deliver at least one bioelectric signal from the bioelectric signal generator to the heart valve to stimulate regeneration of the heart valve.

2. The system of claim 1, further comprising at least one active aspiration device.

3. The system of claim 1, wherein at least one bioelectric signal prevents re-calcification of the heart valve.

4. The system of claim 3, further comprising a deployable net apparatus configured to encompass at least a portion of a heart valve.

5. The system of claim 4, wherein the deployable net apparatus is comprised of electrospun polymers forming a nanoscale fiber mesh.

6. The system of claim 1, wherein the at least one mechanical decalcification device comprises an ultrasonic device.

7. The system of claim 1, further comprising a biocompatible solvent delivery device configured for delivering a stream of biocompatible solvent to a heart valve.

8. The system of claim 1, further comprising:
   a micro infusion pump configured to deliver a regeneration cocktail composition to the heart valve.

9. The system of claim 8, further comprising a nitinol ring placement catheter.

10. The system of claim 1, wherein the bioelectric signal(s) upregulate(s) expression of tropoelastin and/or klotho.

11. A method of heart valve decalcification in a patient, the method comprising:
    mechanically removing calcium deposits on a heart valve utilizing the catheter system of claim 1, and
    applying at least one bioelectric signal to the heart valve from the catheter system's bioelectric signal array.

12. The method of claim 11, further comprising removing debris via suction.

13. The method of claim 11, further comprising removing calcium deposits on the heart valve by directing a stream of biocompatible solvent onto the heart valve.

14. The method of claim 13, further comprising bathing the heart valve with a biochemical bath to encourage healing and regeneration of tissue.

15. The method of claim 14, further comprising: placing a nitinol ring in the patient to reform the shape of the heart valve by installing a nitinol ring.

16. The method of claim 15, further comprising placing autologous cell created heart valve leaflets.

17. The method of claim 11, wherein mechanically removing calcium deposits on the heart valve comprises mechanically removing the calcium deposits on the heart valve with a bur.

18. The method of claim 11, wherein mechanically removing calcium deposits on the heart valve comprises mechanically removing the calcium deposits on the heart valve with an ultrasonic device.

19. The method of claim 11, wherein mechanically removing calcium deposits on the heart valve comprises mechanically removing the calcium deposits on the heart valve with a handheld mechanical decalcification device comprising a bur extending from a hand piece.

20. The method according to claim 11, further comprising:
   infusing elastin nanoparticles into the subject.

* * * * *